US011819554B2

(12) United States Patent
Green et al.

(10) Patent No.: US 11,819,554 B2
(45) Date of Patent: Nov. 21, 2023

(54) COMPOSITIONS AND METHODS FOR MODULATING FMR1 EXPRESSION

(71) Applicant: University of Massachusetts, Boston, MA (US)

(72) Inventors: Michael R. Green, Boylston, MA (US); Minggang Fang, Worcester, MA (US); Walter Kowtoniuk, South Boston, MA (US)

(73) Assignees: UNIVERSITY OF MASSACHUSETTS, Boston, MA (US); FULCRUM THERAPEUTICS, INC., Cambridge, MA (US)

( * ) Notice: Subject to any disclaimer, the term of this patent is extended or adjusted under 35 U.S.C. 154(b) by 1076 days.

(21) Appl. No.: 15/760,765

(22) PCT Filed: Sep. 16, 2016

(86) PCT No.: PCT/US2016/052294
§ 371 (c)(1),
(2) Date: Mar. 16, 2018

(87) PCT Pub. No.: WO2017/049192
PCT Pub. Date: Mar. 23, 2017

(65) Prior Publication Data
US 2018/0256749 A1   Sep. 13, 2018

Related U.S. Application Data

(60) Provisional application No. 62/220,202, filed on Sep. 17, 2015.

(51) Int. Cl.
| A61K 31/711 | (2006.01) |
| A61K 35/30 | (2015.01) |
| A61K 38/45 | (2006.01) |
| A61K 38/53 | (2006.01) |
| A61K 39/395 | (2006.01) |
| A61K 48/00 | (2006.01) |
| A61K 31/5377 | (2006.01) |
| A61K 31/549 | (2006.01) |
| A61K 31/706 | (2006.01) |
| A61K 31/713 | (2006.01) |
| C12Q 1/6883 | (2018.01) |
| C12N 15/113 | (2010.01) |
| A61K 31/7088 | (2006.01) |
| A61K 31/404 | (2006.01) |
| A61K 31/546 | (2006.01) |
| A61K 31/167 | (2006.01) |
| A61K 31/497 | (2006.01) |
| A61K 31/506 | (2006.01) |
| A61K 31/437 | (2006.01) |
| A61K 31/4406 | (2006.01) |

(Continued)

(52) U.S. Cl.
CPC .......... *A61K 48/005* (2013.01); *A61K 31/167* (2013.01); *A61K 31/404* (2013.01); *A61K 31/437* (2013.01); *A61K 31/4406* (2013.01); *A61K 31/496* (2013.01); *A61K 31/497* (2013.01); *A61K 31/506* (2013.01); *A61K 31/522* (2013.01); *A61K 31/5377* (2013.01); *A61K 31/546* (2013.01); *A61K 31/549* (2013.01); *A61K 31/706* (2013.01); *A61K 31/7088* (2013.01); *A61K 31/711* (2013.01); *A61K 31/713* (2013.01); *A61K 31/7105* (2013.01); *A61K 35/30* (2013.01); *A61K 38/45* (2013.01); *A61K 38/53* (2013.01); *A61K 39/3955* (2013.01); *A61K 48/0016* (2013.01); *A61P 15/02* (2018.01); *A61P 25/14* (2018.01); *C12N 15/113* (2013.01); *C12Q 1/6883* (2013.01); *C12N 2310/11* (2013.01); *C12N 2310/14* (2013.01); *C12N 2310/141* (2013.01); *C12N 2310/531* (2013.01); *C12Q 2600/154* (2013.01); *C12Q 2600/158* (2013.01); *C12Y 201/01037* (2013.01); *C12Y 201/01043* (2013.01); *C12Y 603/02019* (2013.01)

(58) Field of Classification Search
CPC .................................................... A61K 48/005
See application file for complete search history.

(56) References Cited

U.S. PATENT DOCUMENTS 4,576,957 A      3/1986   Marsico et al.
2010/0279293 A1  11/2010  Tapscott et al.
(Continued)

FOREIGN PATENT DOCUMENTS

WO   WO-2005009349 A2 *  2/2005   ......... A61K 31/7068
WO   WO 2007/058927 A1    5/2007
(Continued)

OTHER PUBLICATIONS

Bagni C, Tassone F, Neri G, Hagerman R. Fragile X syndrome: causes, diagnosis, mechanisms, and therapeutics. The Journal of clinical investigation. Dec. 3, 2012;122(12):4314-22. (Year: 2012).*
(Continued)

*Primary Examiner* — Allison M Fox
*Assistant Examiner* — Jennifer S Spence
(74) *Attorney, Agent, or Firm* — CANTOR COLBURN LLP

(57) ABSTRACT

The disclosure relates to methods and compositions for reactivating a silenced FMR1 gene. In some aspects, methods described by the disclosure are useful for treating a FMR1-inactivation-associated disorder (e.g., fragile X syndrome).

10 Claims, 30 Drawing Sheets
Specification includes a Sequence Listing.

(51) Int. Cl.
  *A61K 31/522* (2006.01)
  *A61K 31/496* (2006.01)
  *A61P 25/14* (2006.01)
  *A61P 15/02* (2006.01)
  *A61K 31/7105* (2006.01)

(56) References Cited

U.S. PATENT DOCUMENTS

| | | |
|---|---|---|
| 2013/0236536 A1 | 9/2013 | Phiasivongsa et al. |
| 2015/0038496 A1* | 2/2015 | Amigorena ............... A61P 1/04 514/222.8 |

FOREIGN PATENT DOCUMENTS

| | | | |
|---|---|---|---|
| WO | WO 2009/045467 A1 | 4/2009 | |
| WO | WO 2012/174610 A1 | 12/2012 | |
| WO | WO 2015/128837 A1 | 9/2015 | |
| WO | WO-2016073956 A1 * | 5/2016 | ........... C07D 519/00 |

OTHER PUBLICATIONS

Varela MA, Roberts TC, Wood MJ. Epigenetics and ncRNAs in brain function and disease: mechanisms and prospects for therapy. Neurotherapeutics. Oct. 2013; 10(4):621-31. (Year: 2013).*
Kumari D, Usdin K. Polycomb group complexes are recruited to reactivated FMR1 alleles in Fragile X syndrome in response to FMR1 transcription. Human molecular genetics. Dec. 15, 2014;23(24):6575-83. (Year: 2014).*
Kumari D, Usdin K. The distribution of repressive histone modifications on silenced FMR1 alleles provides clues to the mechanism of gene silencing in fragile X syndrome. Human molecular genetics. Dec. 1, 2010;19(23):4634-42. (Year: 2010).*
Sandi C, Sandi M, Anjomani Virmouni S, Al-Mahdawi S, Pook MA. Epigenetic-based therapies for Friedreich ataxia. Frontiers in genetics. Jun. 3, 2014;5:165. (Year: 2014).*
Fiskus W, Wang Y, Sreekumar A, et al. Combined epigenetic therapy with the histone methyltransferase EZH2 inhibitor 3-deazaneplanocin A and the histone deacetylase inhibitor panobinostat against human AML cells. Blood, The Journal of the American Society of Hematology. Sep. 24, 2009;114(13):2733-43. (Year: 2009).*
Fillmore CM, Xu C, Desai PT, Berry JM, Rowbotham SP, Lin YJ, Zhang H, Marquez VE, Hammerman PS, Wong KK, Kim CF. EZH2 inhibition sensitizes BRG1 and EGFR mutant lung tumours to TopoII inhibitors. Nature. Apr. 2015;520(7546):239-42. (Year: 2015).*
Coffee B, Zhang F, Ceman S, Warren ST, Reines D. Histone modifications depict an aberrantly heterochromatinized FMR1 gene in fragile x syndrome. Am J Hum Genet. 2002;71(4):923-932 (Year: 2002).*
Yandim C, Natisvili T, Festenstein R. Gene regulation and epigenetics in Friedreich's ataxia. Journal of neurochemistry. Aug. 2013; 126:21-42. (Year: 2013).*
Kumari et al. Polycomb group complexes are recruited to reactivated FMR1 alleles in fragile X syndrome in response to FMR1 transcription. Human Molecular Genetics 2014,:1-9. (Year: 2014).*
Francis Crick Institute webpage (https://www.crick.ac.uk/research/research-reports/neurogenesis-in-the-adult-mouse-brain), captured Jul. 24, 2021, 1-6. (Year: 2021).*

Ladd et al. An antisense transcript spanning the CGG repeat region of FMR1 is upregulated in premutation carriers but silenced in full mutation individuals. Human Molecular Genetics 2007, 16;24:3174-3187. (Year: 2007).*
Onder et al. Chromatin-modifying enzymes as modulators of reprogramming. Nature 2012, 483:598-602. (Year: 2012).*
Fillmore et al. EZH2 inhibition sensitizes BRG1 and EGFR mutant lung tumors to TopoII inhibitors. Nature 2015, 520:239-242. (Year: 2015).*
Extended European Search Report for Application No. EP 16847468. 2, dated Mar. 21, 2019.
Bar-Nur et al., Molecular analysis of FMR1 reactivation in fragile-X induced pluripotent stem cells and their neuronal derivatives. J Mol Cell Biol. Jun. 2012;4(3):180-3. doi: 10.1093/jmcb/mjs007. Epub Mar. 19, 2012.
Dev et al., 5-azacytidine decreases the frequency of fragile X expression in peripheral lymphocyte culture. Am J Med Genet. Jan. 1984;17(1):253-4. doi: 10.1002/ajmg.1320170116.
Kaufmann et al., High-Throughput Screening Using iPSC-Derived Neuronal Progenitors to Identify Compounds Counteracting Epigenetic Gene Silencing in Fragile X Syndrome. J Biomol Screen. Oct. 2015;20(9):1101-11. doi: 10.1177/1087057115588287. Epub May 29, 2015.
Kumari et al., Sustained expression of FMR1 mRNA from reactivated fragile X syndrome alleles after treatment with small molecules that prevent trimethylation of H3K27. Hum Mol Genet. Sep. 1, 2016;25(17):3689-3698. doi: 10.1093/hmg/ddw215. Epub Jul. 4, 2016.
Sayegh et al., Identification of small molecule inhibitors of Jumonji AT-rich interactive domain 1B (JARID1B) histone demethylase by a sensitive high throughput screen. J Biol Chem. Mar. 29, 2013;288(13):9408-17. doi: 10.1074/jbc.M112.419861. Epub Feb. 13, 2013.
Todd et al., Histone deacetylases suppress CGG repeat-induced neurodegeneration via transcriptional silencing in models of fragile X tremor ataxia syndrome. PLoS Genet. Dec. 9, 2010;6(12):e1001240. doi: 10.1371/journal.pgen.1001240.
[No Author Listed] LMK-235 Catalog No. S7569. Selleeckchem. com Apr. 24, 2015.
Chiurazzi et al., Synergistic effect of histone hyperacetylation and DNA demethylation in the reactivation of the FMR1 gene. Hum Mol Gen. Nov. 1999;8(12):2317-2323.
Ghoshal et al., 5-Aza-deoxycytidine induces selective degradation of DNA methyltransferase 1 by a proteasomal pathway that requires the KEN box, bromo-adjacent homology domain, and nuclear localization signal. Mol Cell Biol. Jun. 2005;25(11):4727-41. Erratum in: Mol Cell Biol. Apr. 30, 2018;38(10 ):.
Ismail et al., A small molecule inhibitor of polycomb repressive complex 1 inhibits ubiquitin signaling at DNA double-strand breaks. J Biol Chem. Sep. 13, 2013;288(37):26944-54. doi: 10.1074/jbc. M113.461699. Epub Jul. 30, 2013.
Azechi et al., 5-aza-2'-Deoxycytidine, a DNA methyltransferase inhibitor, facilitates the inorganic phosphorus-induced mineralization of vascular smooth muscle cells. J Atheroscler Thromb. 2014;21(5):463-76. doi: 10.5551/jat.20818. Epub Jan. 20, 2014.
Chen et al., DNA methyltransferases 1 and 3B are required for hepatitis C virus infection in cell culture. Virology. Jun. 20, 2013;441(1):57-65. doi: 10.1016/j.virol.2013.03.005. Epub Mar. 29, 2013.
Tennis et al., Methylation of Wnt7a is modulated by DNMT1 and cigarette smoke condensate in non-small cell lung cancer. PLoS One. 2012;7(3):e32921. doi: 10.1371/journal.pone.0032921. Epub Mar. 5, 2012.

* cited by examiner

SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 1
atccatcaga atgtattcgg c                                                    21

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
ttgatgtcag tctcattggg c                                                    21

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 3
gcagctggtg agaaggcaat a                                                    21

<210> SEQ ID NO 4
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 4
tttggtccca attaacctag c                                                    21

<210> SEQ ID NO 5
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 5
ttgtggcaaa gaaagcgatg c                                                    21

<210> SEQ ID NO 6
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 6
aataggccat gaatcccaac g                                                    21

<210> SEQ ID NO 7
<211> LENGTH: 21
<212> TYPE: DNA
<213> ORGANISM: Artificial Sequence

```
<220> FEATURE:
<223> OTHER INFORMATION: Synthetic Oligonucleotide

<400> SEQUENCE: 7
tttggtccgt tgttactag g                                               21

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 8
ttctaaagct aacctcacag c                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 9
ttaaaggtgc taataacagt c                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 10
atctcgatga ctttctctag c                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 11
tgcggtgtca tttctgcggt g                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 12
tagcccgtgt ttctgcttgg c                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 13
aaacctgaat ctgttcgtag c                                              21
```

```
<210> SEQ ID NO 14
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 14
aaatctggtt tcgtgtggac g                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 15
aatgcgttcg taatgtgatc g                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 16
aacagactga tctagcactg g                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 17
aaacaatgcg ttcgtagtgg g                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 18
ttaggtgccg tttactgtca c                                              21
```

COMPOSITIONS AND METHODS FOR MODULATING FMR1 EXPRESSION

RELATED APPLICATIONS

This application is a National Stage Application of PCT/US2016/052294, filed Sep. 16, 2016 entitled "COMPOSITIONS AND METHODS FOR MODULATING FMR1 EXPRESSION", which claims the benefit under 35 U.S.C. § 119(e) of the filing date of U.S. Provisional Patent Application No. 62/220,202, filed on Sep. 17, 2015, entitled "COMPOSITIONS AND METHODS FOR MODULATING FMR1 EXPRESSION", the entire contents of each application which are incorporated herein by reference.

FIELD OF THE DISCLOSURE

The invention relates to methods for modulating gene expression.

BACKGROUND OF INVENTION

Fragile X Syndrome (FXS) is a genetic condition that causes a range of developmental problems including learning disabilities and cognitive impairment. FXS is the most common genetic form of mental retardation, and occurs in approximately 1 in 4,000 males and 1 in 8,000 females. Usually, males are more severely affected by this disorder than females. Most males with FXS have mild to moderate intellectual disability, while about one-third of affected females are intellectually disabled.

FXS is caused by the expansion (>200 repeats) of a polymorphic CGG sequence within the 5' untranslated region (UTR) of the X-linked FMR1 gene. The FMR1 gene bearing the expanded CGG repeat becomes transcriptionally silenced, resulting in a lack of the Fragile X mental retardation protein (FMRP). FMRP is an RNA-binding protein and a translational repressor that modulates the translation of numerous synaptic proteins, and plays an important role in synaptic plasticity.

Several therapeutic agents that target the underlying mechanisms of FXS have been developed. Some of these targeted treatments have demonstrated efficacy across multiple features of FXS in the knockout mouse model. However, effective human treatments remain needed. To date, no specific therapy exists for FXS, and current treatments are only directed to improve behavioral symptoms. Thus, there is a general need for the development of novel compositions and methods for treating FXS.

SUMMARY OF INVENTION

In some aspects, the disclosure relates to epigenetic modulators useful for the treatment of diseases associated with FMR1-inactivation-associated disorders (e.g., FXS). In some embodiments, epigenetic modulators disclosed herein are useful because they induce a more permissive chromatin state in the epigenetically-silenced FMR1 gene. Without wishing to be bound by any particular theory, inducing a more permissive chromatin state in the epigenetically-silenced FMR1 gene of subjects having FMR1 inactivation-associated disorders (e.g., FXS) is expected to result in increased FMR1 expression (e.g., reactivation of FMR1) and thereby decrease disease symptomatology or reverse disease symptoms. In some embodiments, reactivation of the silenced FMR1 gene is expected to reverse disease symptoms. Moreover, in some embodiments, asymptomatic carriers of a pre-mutation, and rare asymptomatic individuals who have a full mutation but FMR1 is not silenced, have fragile X mental retardation protein (FMRP) levels that are lower than that of normal individuals. Thus, in some embodiments, even a modest reactivation of the silenced FMR1 gene according to methods provided herein may have substantial therapeutic benefit.

Aspects of the invention relate to the discovery that inhibition of certain regulators of the FMR1 gene by epigenetic modulators (e.g., selective inhibitors) results in reactivation of the epigenetically-silenced FMR1 gene. For example, selective inhibition of DNMT1, SUV39H1, EHZ2, RING1B/RNF2, certain histone deacetylases (e.g., HDAC5, HDAC10, SIRT5), and/or certain histone demethylases (e.g., KDM5C, KDM5D) results in reactivation of the transcriptionally-inactive FMR1 gene. Thus, in some embodiments, selective inhibition of epigenetic regulators of the FMR1 gene reactivates transcriptionally-silenced FMR1 and is thus useful for treating FMR1-inactivation-associated disorders, such as fragile X syndrome (FXS).

Accordingly, aspects of the disclosure relate to methods of reactivating the epigenetically-silenced FMR1 gene in a subject. In some embodiments, the methods involve administering to the subject an epigenetic modulator of one of the following: DNMT1, SUV39H1, EHZ2, RING1B/RNF2, HDAC5, HDAC10, SIRT5, KDM5C and KDM5D.

In some embodiments, the epigenetic modulator selectively inhibits DNMT1 (e.g., 5-azacytidine, F6363-1015).

In some embodiments, the epigenetic modulator selectively inhibits SUV39H1 (e.g., chaetocin, F2740-0099, F6403-3095, F5599-0533).

In some embodiments, the epigenetic modulator selectively inhibits EZH2 (e.g., EPZ6438, GSK126, F2880-2560).

In some embodiments, the epigenetic modulator selectively inhibits RING1B/RNF2 (e.g., PRT4165).

In some embodiments, the epigenetic modulator of FMR1 is an inhibitor of a histone deacetylase (HDAC). In some embodiments, the epigenetic modulator selectively inhibits HDAC5 (e.g., F6196-0976), HDAC10 (e.g., F6196-0976), SIRT5.

In some embodiments, the epigenetic modulator of FMR1 is an inhibitor of a histone demethylase. In some embodiments, the epigenetic modulator selectively inhibits KDM5C or KDM5D.

In some aspects, the disclosure provides a method for treating a FMR1-inactivation-associated disorder in a subject in need thereof, the method comprising: administering to the subject a therapeutically effective amount of an epigenetic modulator of FMR1, wherein the epigenetic modulator reactivates FMR1 in the subject.

In some embodiments, the FMR1-inactivation-associated disorder is FXS.

In some aspects, the disclosure provides a method for reactivating a transcriptionally inactive FMR1 gene in a cell, the method comprising: contacting the cell with an effective amount of an epigenetic modulator of FMR1, wherein the epigenetic modulator reactivates FMR1 in the cell.

In some embodiments, the epigenetic modulator of FMR1 is an inhibitor of a methyltransferase. In some embodiments, the methyltransferase is a DNA methyltransferase. In some embodiments, the DNA methyltransferase is selected from the group consisting of: DNMT1, DNMT3A, and DNMT3B. In some embodiments, the methyltransferase is a histone methyltransferase. In some embodiments, the histone methyltransferase is selected from the group consisting of: EZH2, SETDB1, EHMT1/GLP, EHMT2/G9a, SUV39H1, SUV420H1, and SUV420H2

In some embodiments, the epigenetic modulator of FMR1 is an inhibitor of a histone ubiquitin ligase. In some embodiments, the histone ubiquitin ligase is a ubiquitin ligase that ubiquitinates histone H2A. In some embodiments, the histone ubiquitin ligase is RING1B/RNF2.

In some embodiments, the epigenetic modulator of FMR1 is an inhibitor of a histone modifying factor associated with loss of or absence of histone modifications indicative of active chromatin at the FMR1 gene. Accordingly, in some embodiments, use of the epigenetic modulator of FMR1 results in the presence of histone modifications indicative of active chromatin at the FMR1 gene. In some embodiments, the histone modification indicative of active chromatin is acetylation of at least one histone selected from the group consisting of: H2A, H2B, H3, and H4. In some embodiments, the histone modification is trimethylation of histone H3 lysine 4 (H3K4me3). In some embodiments, the histone modification is histone H2A acetylation (e.g., at lysine 5), histone H2B acetylation (e.g., at lysine 5, 12, 15 or 20), histone H3 acetylation (e.g., at lysine 4), histone H4 acetylation (e.g., at lysine 8).

In some embodiments, the epigenetic modulator of FMR1 targets at least one of the following: a histone deacetylase (e.g., HDAC1, HDAC2, HDAC3, HDAC4, HDAC5, HDAC6, HDAC7, HDAC8, HDAC9, HDAC10, SIRT1, SIRT2, SIRT3, SIRT4, SIRT5, SIRT6, SIRT7) and a demethylase (e.g., KDM5A, KDM5B, KDM5C, or KDM5D).

In some embodiments, the epigenetic modulator of FMR1 is a nucleic acid, polypeptide, or small molecule.

In some embodiments, the epigenetic modulator of FMR1 is a nucleic acid. In some embodiments, the nucleic acid is an interfering nucleic acid selected from the group consisting of: double stranded RNA (dsRNA), siRNA, shRNA, miRNA, and antisense oligonucleotide (ASO). In some embodiments, the interfering nucleic acid is an shRNA listed in Table 2. In some embodiments, the interfering nucleic acid is an ASO having a sequence as listed in Table 2.

In some embodiments, the epigenetic modulator of FMR1 is a polypeptide, for example an antibody.

In some embodiments, the epigenetic modulator of FMR1 is a small molecule, for example a small molecule listed in Table 1.

In some embodiments, a subject is identified as being in need of treatment with the epigenetic modulator based upon the presence of a transcriptionally inactive FMR1 gene. In some embodiments, the transcriptionally inactive FMR1 gene is epigenetically silenced.

In some embodiments, the transcriptionally inactive FMR1 gene comprises at least one epigenetic mark associated with silenced FMR1 gene. In some embodiments, at least one epigenetic mark is selected from the group consisting of DNA methylation (DNAme), histone H3 lysine 27 trimethylation (H3K27me3), histone H3 lysine 9 trimethylation (H3K9me3), histone 4 lysine 20 trimethylation (H4K20me3), histone H2A ubiquitination (H2Aub).

In some embodiments, the subject is identified as being in need of treatment based upon the presence of an expansion of a polymorphic CGG repeat within the 5'UTR of the FMR1 gene. In some embodiments, the expansion comprises between about 55 CGG repeats and about 200 CGG repeats. In some embodiments, the expansion comprises more than 200 CGG repeats.

In some embodiments, an effective amount of epigenetic modulator of FMR1 is delivered to the CNS, testes, ovaries, esophageal epithelium, thymus, eye, or spleen of the subject.

In some embodiments, the effective amount of epigenetic modulator of FMR1 is delivered to the CNS of the subject. In some embodiments, the effective amount of epigenetic modulator of FMR1 is delivered to neuronal cells. In some embodiments, the neuronal cells are differentiated neuronal cells.

In some embodiments, an effective amount of epigenetic modulator of FMR1 is delivered to an induced pluripotent stem cell (iPSC). In some embodiments, the cell (e.g., neuronal cell, iPSC, neural progenitor cells (NPCs)) is in vitro. In some embodiments, the cell comprises an expansion of a polymorphic CGG repeat within the 5'UTR of the FMR1 gene, for example an expansion that comprises between about 55 and about 200 CGG repeats. In some embodiments, the cell comprises an expansion that comprises more than 200 CGG repeats.

In some embodiments, the epigenetic modulator inhibits formation of an R-loop between the FMR1 gene and an mRNA encoding FMR1.

In some embodiments, methods described by the disclosure further comprise assessing the FMR1 epigenetic profile of the subject before and/or after administering an epigenetic modulator of FMR1, wherein a change in the FMR1 epigenetic profile indicates effectiveness of the treatment.

In some aspects, the disclosure provides a method for identifying epigenetic modulators of FMR1, the method comprising: contacting a cell comprising an inactivated FMR1 gene with a candidate agent; detecting the expression level of FMR1 in the cell; and, identifying the candidate agent as an epigenetic modulator of FMR1 when the expression level of FMR1 increases relative to a control cell after contact with the candidate agent.

In some embodiments, the method is performed in vitro, for example on a cell (e.g., neuronal cell, iPSC, neural progenitor cells (NPCs)). In some embodiments, the cell has an epigenetically silenced FMR1 gene. In some embodiments, the cell comprises an expansion of a polymorphic CGG repeat within the 5'UTR of the FMR1 gene, for example an expansion that comprises between about 55 and about 200 CGG repeats. In some embodiments, the cell comprises an expansion that comprises more than 200 CGG repeats. The cell comprises, in some embodiments, at least one epigenetic mark associated with silenced FMR1 gene.

In some embodiments, the candidate agent is a nucleic acid, polypeptide, or small molecule. In some embodiments, the candidate agent is a nucleic acid. In some embodiments, the nucleic acid is an interfering nucleic acid selected from the group consisting of: double stranded RNA (dsRNA), siRNA, shRNA, miRNA, and antisense oligonucleotide (ASO). In some embodiments, the candidate agent is a small molecule. In some embodiments, the candidate agent is a polypeptide. In some embodiments, the polypeptide is an antibody.

In some embodiments, the candidate agent is selected from a compound library. In some embodiments, the library comprises methyltransferase inhibitors. In some embodiments, the library consists of methyltransferase inhibitors. In some embodiments, the methyltransferase inhibitors are DNA methyltransferase inhibitors. In some embodiments, the methyltransferase inhibitors are histone methyltransferase inhibitors.

In some embodiments, the library comprises histone ubiquitin ligase inhibitors. In some embodiments, the library consists of histone ubiquitin ligase inhibitors. In some embodiments, the histone ubiquitin ligase is a ubiquitin ligase that ubiquitinates histone H2A.

In some embodiments, the candidate agent is an inhibitor of a histone modifying factor associated with loss of or absence of histone modifications indicative of active chromatin at the FMR1 gene. In some embodiments, the histone modification indicative of active chromatin is acetylation of at least one histone selected from the group consisting of: H2A, H2B, H3, and H4. In some embodiments, the histone modification is trimethylation of histone H3 lysine 4 (H3K4me3).

In some embodiments, the candidate agent targets (e.g., inhibits) at least one of the following: HDAC1, HDAC2, HDAC3, HDAC4, HDAC5, HDAC6, HDAC7, HDAC8, HDAC9, HDAC10, SIRT1, SIRT2, SIRT3, SIRT4, SIRT5, SIRT6, SIRT7, KDM5A, KDM5B, KDM5C, or KDM5D.

In some embodiments, detection is performed by hybridization-based assay, Western blot, flow cytometry, quantitative real-time polymerase chain reaction (qRT-PCR), chromatin immunoprecipitation (ChIP), FACS, bisulfite sequencing, immunofluorescence, etc.

BRIEF DESCRIPTION OF DRAWINGS

FIG. 6A shows qRT-PCR analysis monitoring expression of FMR1 in FXS iPSCs expressing an FMR1-SF shRNA. The results were normalized to that obtained in wild-type iPSCs (BJ1-iPS4 cells), which was set to 1.
FIG. 6B shows an immunoblot analysis showing FMRP protein levels in FXS iPSCs expressing an FMR1-SF shRNA. The levels of FMRP in wild-type iPSCs, diluted 2-fold (representing the level of FMRP at 50% of wild-type), 4-fold (25%) and 8-fold (12.5%) are shown. Tubulin was monitored as a loading control.
FIG. 6C shows qRT-PCR analysis monitoring expression of FMR1 in FXS SC135 iPSCs expressing an FMR1-SF shRNA. The results were normalized to that obtained with a control non-silencing (NS) shRNA, which was set to 1.
FIG. 6D shows an immunoblot analysis showing FMRP protein levels in FXS SC135 iPSCs expressing an FMR1-SF shRNA. The levels of FMRP in wild-type iPSCs, diluted 8-fold (12.5%) and 16-fold (6.25%) are shown.
FIG. 6E shows bisulfite sequencing analysis of the FMR1 promoter in FXS iPSCs (FXS 848-iPS3 cells) treated with DMSO or 5-azacytine (5-aza), or with an NS or FMR1-SF shRNA. (Top) Schematic of the FMR1 promoter; positions of CpGs are shown to scale by vertical lines. (Bottom) Each circle represents a methylated (black) or unmethylated (white) CpG dinucleotide. Each row represents a single clone. Data are represented as mean±SD.

FIGS. 7A-7G shows the FMR1-SFs stably associate with epigenetically silenced FMR1 through an ordered pathway. FIG. 7A shows ChIP analysis monitoring binding of FMR1-SFs to the FMR1 promoter in wild-type (WT) and FXS iPSCs (FXS 848-iPS3 cells). As a negative control, binding was also monitored at the constitutively-expressed APRT promoter. The results were normalized to that obtained with IgG, which was set to 1. FIG. 7B shows ChIP analysis monitoring binding of the FMR1-SFs in FXS iPSCs expressing an shRNA targeting each FMR1-SF. FIG. 7C shows a summary of the ordered pathway in which FMR1-SFs bind to the FMR1 promoter. For steps at which the order of cofactors cannot be distinguished, the cofactors are aligned horizontally. FIG. 7D shows ChIP analysis monitoring the levels of H3K9me3 and H3K27me3 on the silenced FMR1 promoter in FXS iPSCs. FIG. 7E shows H3K27me3 ChIP analysis in FXS iPSCs expressing an FMR1-SF shRNA. FIG. 7F shows H3K9me3 ChIP analysis in FXS iPSCs expressing an FMR1-SF shRNA. Data are represented as mean±SD.

FIG. 8A shows a qRT-PCR analysis monitoring expression of FMR1 in FXS iPSCs treated with 5-aza, chaetocin, EPZ6438, GSK126, PRT4165 or, as a control, DMSO. The results were normalized to that obtained in wild-type iPSCs (BJ1-iPS4 cells), which was set to 1. FIG. 8B is an immunoblot analysis showing FMRP protein levels in FXS iPSCs treated with 5-aza, chaetoxin, EPZ6438, GSK126 or PRT4165. The levels of FMRP in wild-type iPSCs are shown. Tubulin was monitored as a loading control. FIG. 8C shows a qRT-PCR analysis monitoring expression of FMR1 in FXS iPSCs treated with chaetoxin, EPZ6438 or PRT4165, either alone or in pair-wise combinations. The results were normalized to that obtained with DMSO, which was set to 1. FIG. 8D shows a qRT-PCR analysis monitoring FMR1 expression in FXS iPSCs treated with increasing concentrations of EPZ6438. FIG. 8E shows a qRT-PCR analysis monitoring FMR1 expression in FXS iPSCs following EPZ6438 addition (top) or withdrawal (bottom). FIG. 8F shows a ChIP analysis monitoring DNMT1 binding to the FMR1 promoter in FXS iPSCs following EPZ6438 addition (top) or withdrawal (bottom). Data are represented as mean±SD.

FIG. 9A shows a qRT-PCR analysis monitoring FMR1 expression in FXS iPSCs treated with FMR1-SF inhibitors obtained from the Epigenetics Targeted Library (Life Chemicals). FIG. 9B shows reactivation curves for each of the six positive compounds. FIG. 9C shows structures of positive compounds. FIG. 9D shows a summary of all small molecule inhibitors identified to date that reactivate silenced FMR1. Data are represented as mean±SD.

FIG. 10A shows a qRT-PCR analysis monitoring FMR1 expression in FXS NPCs expressing a NS or FMR1-SF shRNA. FIG. 10B shows an immunoblot analysis showing FMRP levels in FXS NPCs expressing a NS or FMR1-SF shRNA. The levels of FMRP in wild-type iPSCs, diluted 2-fold (50%), 4-fold (25%) and 8-fold (12.5%) are shown. Tubulin was monitored as a loading control. FIG. 10C shows a qRT-PCR analysis monitoring FMR1 expression in FXS NPCs treated with 5-aza, chaetocin, EPZ6438, GSK126, PRT4165 or, as a control, DMSO. FIG. 10D shows an immunoblot analysis showing FMRP levels in FXS NPCs treated with 5-aza, chaetocin, EPZ6438, GSK126 or PRT4165. The levels of FMRP in wild-type iPSCs are shown. Data are represented as mean±SD.

FIG. 11A depicts immunofluorescence showing expression of neuronal markers MAP2 and NeuN in post-mitotic neurons derived from FXS 848-NPCs. FIG. 11B presents images showing lack of staining with an antibody directed the mitotic marker phosphorylated H3 in post-mitotic neurons. FIG. 11C shows a qRT-PCR analysis monitoring FMR1 expression in FXS neurons expressing a NS or FMR1-SF shRNA. FIG. 11D shows an immunoblot analysis showing FMRP levels in FXS neurons expressing a NS or FMR1-SF shRNA. The levels of FMRP in wild-type iPSCs are shown. FIG. 11E shows a qRT-PCR analysis monitoring FMR1 expression in FXS neurons treated with 5-aza, chaetocin, EPZ6438, GSK126, PRT4165 or, as a control, DMSO. FIG. 11F shows an immunoblot analysis showing FMRP levels in FXS neurons treated with 5-aza, chaetocin, EPZ6438, GSK126 or PRT4165. The levels of FMRP in wild-type iPSCs are shown. FIG. 11G shows a qRT-PCR analysis monitoring FMR1 expression in FXS neurons following EPZ6438 addition (top) or withdrawal (bottom). Data are represented as mean±SD.

FIG. 12A shows a qRT-PCR analysis monitoring REST expression in FXS neurons expressing a FMR1-SF shRNA or treated with an FMR1-SF inhibitor. The expression of FMR1 in wild-type neurons are shown. FIG. 12B shows a qRT-PCR analysis monitoring expression of REST target genes ROBO3, SLIT1 and DCC in FXS neurons expressing a FMR1-SF shRNA or treated with an FMR1-SF inhibitor. The expression of each gene in wild-type neurons are shown. FIG. 12C shows an immunoblot analysis showing FMRP levels in FXS neurons expressing an FMR1-SF shRNA or with an FMR1-SF inhibitor. The levels of FMRP in wild-type neurons are shown. FIG. 12D depicts immunofluorescence showing TUJ1 and FMRP staining in FXS neurons expressing an FMR1-SF shRNA. DAPI staining is shown in blue. Merged images are shown. Enlarged images of the TUJ1 staining are shown on the right. FIG. 12E depicts immunofluorescence showing TUJ1 and FMRP staining in FXS neurons treated with an FMR1-SF inhibitor. DAPI staining is shown. Merged images are shown. Enlarged images of the TUJ1 staining are shown on the right. FIG. 12F shows the quantification of neurite process length in FXS neurons expressing a FMR1-SF1 shRNA or treated with an FMR1-SF inhibitor. The results were normalized to neurite process length in wild-type neurons, which was set to 1. Data are represented as mean±SD.

DETAILED DESCRIPTION OF INVENTION

Figure 1:
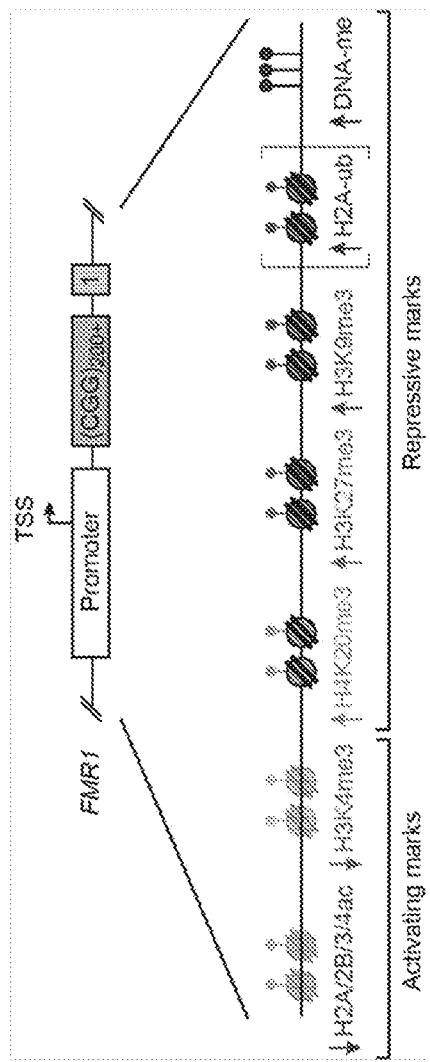
FIG. 1 shows epigenetic marks associated with the silenced FMR1 gene.

In some aspects, the invention relates to the surprising discovery that inducing a more permissive chromatin state in the epigenetically silenced FMR1 gene in patients having FMR1 inactivation-associated disorders (e.g., FXS) may result in increased expression of FMR1 and decreased or reversed disease symptomatology. In some embodiments, methods and compositions described by the disclosure inhibit—for example, through RNA interference (RNAi)-mediated knockdown or small molecule inhibitors—epigenetic silencers of the FMR1 gene. In some embodiments, reactivation of the silenced FMR1 gene is expected to reverse disease symptoms. Moreover, in some embodiments, asymptomatic carriers of a pre-mutation (55-200 CGG repeats), and rare asymptomatic individuals who have a full mutation but FMR1 is not silenced, have FMRP levels that are ~20% that of normal individuals. Thus, in some embodiments, even a modest reactivation of the silenced FMR1 gene according to methods provided herein may have substantial therapeutic benefit. Second, in some embodiments, restoring or improving translational homeostasis in the brain using methods provided herein could ameliorate major symptoms associated with FXS. In some embodiments, elevation of protein synthesis by a mere 15% in the brains of Fmr1 KO mice promotes disease phenotypes, indicating that reducing overall translation by a relatively small amount would be clinically beneficial. Consistent with this observation minocycline, a tetracycline group antibiotic that binds and inhibits prokaryotic and to a lesser extent eukaryotic ribosomes, has resulted in modest but positive outcomes in FXS patients that have been treated with the compound.

Accordingly, in some aspects, the disclosure provides a method for treating a FMR1-inactivation-associated disorder in a subject in need thereof, the method comprising: administering to the subject a therapeutically effective amount of an epigenetic modulator of FMR1, wherein the epigenetic modulator reactivates FMR1 in the subject.

FMR1-Inactivation Associated Disorders

As used herein, the term "FMR1-inactivation-associated disorder" refers to a disease or disorder that results from transcriptional inactivation of the FMR1 gene. Generally, inactivation of the FMR1 gene results in the loss of production of fragile X mental retardation protein (FMRP) and causes a range of developmental problems including learning disabilities and cognitive impairment, moderate to severe mental retardation, ataxia (e.g., loss of coordination), tremor, memory loss, loss of sensation in the lower extremities (e.g., peripheral neuropathy), mental and behavioral changes, and polycystic ovarian syndrome. In some embodiments, an FMR1-inactivation-associated disorders is fragile X syndrome (FXS).

FXS is caused by an expansion of a polymorphic CGG sequence within the 5' untranslated region (5'UTR) of the X-linked FMR1 gene. Without wishing to be bound by any particular theory, the FMR1 gene bearing the expanded CGG repeat becomes transcriptionally silenced due to inhibiting histone modifications and DNA hypermethylation, resulting in a lack of the fragile X mental retardation protein (FMRP). In some embodiments, the FMR1 gene becomes transcriptionally silenced due to the formation of an mRNA-DNA duplex (e.g., an "R-loop") between the expanded CGG repeat of FMR1 mRNA and the complementary CGG repeat of the FMR1 gene.

FXS is the most common inherited form of mental insufficiency and most prevalent monogenic cause of autism, occurring in ~1 in 4,000 males and 1 in 8,000 females. Individuals with FxS display a range of symptoms including low IQ, speech and developmental delays, attention deficit disorder, hand flapping, and seizures. In some embodiments, the syndrome is caused by a CGG repeat expansion in the 5' untranslated region of the X-linked FMR1 gene; when the expansion reaches 200 or more repeats, FMR1 is transcriptionally silenced. In some embodiments, as a consequence, the product of FMR1, the fragile X mental retardation protein (FMRP), is not produced. FMRP is an RNA-binding protein that normally represses mRNA translation in the brain and other tissues; in its absence, protein synthesis is excessive, which results in disease pathology. In some embodiments, the lack of FMRP and elevated protein synthesis is causally linked to synaptic weakening, which is measured electrophysiologically as long-term depression (LTD). In some embodiments, depressed synaptic connectivity causes neural circuit dysfunction and impairment of higher cognitive function such as learning and memory.

Generally, severity of a FMR1-inactivation-associated disorder can be classified by the number of polymorphic CGG repeats present in the 5'UTR of a subject's FMR1 gene. The number of repeats in the expansion can vary. In some embodiments, the number of CGG repeats in the expansion ranges from about 55 to about 500 repeats. In some embodiments, a subject is referred to as "premutation" and the number of CGG repeats ranges from about 55 repeats to about 200 repeats. Premutation subjects are susceptible to conversion to full mutation status and are thus at increased risk of developing FXS compared to subjects having normal alleles (e.g. having between 6 and 54 CGG repeats). In some embodiments, the number of CGG repeats is greater than 200 repeats, and the subject is referred to as having a "full mutation". Full mutation subjects have FXS. In some embodiments, the number of CGG repeats in a subject having FXS ranges from about 201 to about 500 repeats. In some embodiments, the number of CGG repeats is greater than 500 repeats.

There are typically several epigenetic marks associated with a transcriptionally inactive (e.g., silenced) FMR1 gene (FIG. 1). As used herein, the term "epigenetic mark" refers to a feature or characteristic of a gene that is not directly governed by the genetic code, for example methylation of DNA and covalent modification of histone proteins. Generally, epigenetic marks influence the expression of a gene by modifying chromatin state. Epigenetic marks can be activating marks (e.g., promoting expression of the gene) or repressive marks (e.g., inhibiting expression of the gene).

In some aspects, the invention relates to the discovery that there is an increase in several repressive marks on silenced FMR1. Examples of repressive marks detected on silenced FMR1 include, but are not limited to, DNA methylation, histone H3 lysine 27 trimethylation (H3K27me3), histone H3 lysine 9 trimethylation (H3K9me3), and histone H4 lysine 20 trimethylation (H4K20me3). In some embodiments, there is an increase in histone H2A ubiquitination (H2Aub) on silenced FMR1.

In some aspects, the invention relates to the discovery that there is a decrease in activating marks in silenced FMR1. Examples of activating marks not generally detected on silenced FMR1 include, but are not limited to, histone (H2A/2B/3/4) acetylation and histone H3 lysine 4 trimethylation (H3K4me3).

In some aspects, administration of an effective amount of an epigenetic modulator of FMR1 results in the reactivation of FMR1 in a subject. As used herein, the term "reactivation of FMR1" refers to a change in state of a FMR1 gene from a transcriptionally inactive (e.g., silenced) state to a transcriptionally active (e.g., expressed) state. For example, a subject (e.g., a cell in a subject) having a transcriptionally inactive (e.g., silenced) FMR1 gene lacks FMRP; reactivation of FMR1 in the subject (e.g., cell in the subject) leads to expression and production of FMRP. Reactivation of FMR1 can be measured as expression level of FMR1 in a sample (e.g., a cell or a subject) after treatment with an epigenetic modulator of FMR1 relative to expression level of FMR1 in the sample prior to treatment with the epigenetic modulator of FMR1. Reactivation of FMR1 can be measured by any suitable method known in the art, for example by hybridization-based assay (e.g., RT-PCR, qRT-PCR, Northern Blot), protein-based methods (e.g., Western blot), spectroscopic methods (e.g., mass spectrometry), nucleic acid-based methods (e.g., bisulfite sequencing) and cell-based methods (e.g., flow cytometry, fluorescence activated cell sorting (FACS), immunofluorescence).

Epigenetic Modulators of FMR1

As used herein, the term "epigenetic modulator of FMR1" refers to an agent that alters the transcriptional activity of FMR1. For example, in some embodiments an epigenetic modulator of FMR1 increases the transcriptional activity of FMR1. Increased transcriptional activity generally results in increased production of mRNA and/or increased protein translation (e.g., translation of FMRP). In some embodiments, an epigenetic modulator of FMR1 changes the chromatin state of FMR1. An epigenetic modulator can directly alter transcriptional activity of FMR1, or can indirectly alter FMR1 transcriptional activity by interacting with another factor (e.g., protein) that modulate expression and/or the epigenetic state of an FMR1 gene. In some embodiments, an epigenetic modulator of FMR1 inhibits the expression level or activity (e.g., function) of another protein that modulates transcriptional activity of FMR1. For example, in some embodiments, silenced FMR1 has increased DNA methylation by DNA methyltransferase 1 (DNMT1); thus, in some embodiments, an epigenetic modulator of FMR1 is an agent that inhibits DNMT1 activity or expression. In some embodiments, an epigenetic modulator of FMR1 can be a nucleic acid, polypeptide, small molecule, or any combination of the foregoing. An epigenetic modulator may also be referred to herein as an epigenetic modifier.

Figure 2:
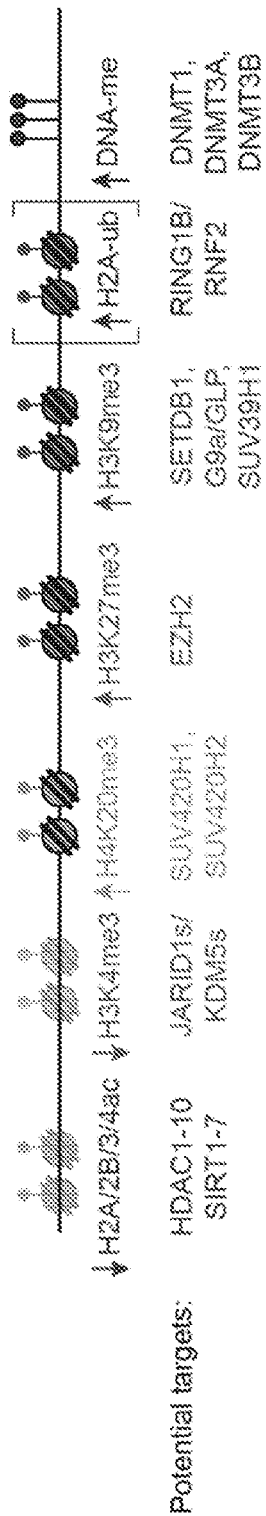
FIG. 2 shows potential targets of epigenetic marks associated with the silenced FMR1 gene.

The chromatin state (e.g., packaging of DNA with histone and non-histone proteins) of a cell has significant effects on gene expression. In some embodiments, the disclosure relates to chromatin modifiers that, when knocked down or inhibited, activate expression of the FMR1 gene in cells (e.g., neuronal cells or iPSCs). In some embodiments, an epigenetic modulator of FMR1 targets such a chromatin modifier. As used herein, the term "chromatin modifier" refers to an agent (e.g., an enzyme or transcription factor) that modifies DNA (e.g., by methylation) or post-translationally modifies histone proteins (for example by phosphorylation, acetylation, methylation or ubiquitination), resulting in alteration of chromatin structure and thus modified gene expression. Examples of chromatin modifiers include, but are not limited to DNA methyltransferases, histone methyltransferases, histone ubiquitin ligases, and histone acetyltransferases. Further examples of chromatin modifiers are shown in FIG. 2.

As used herein, the term "DNA methyltransferase" refers to an enzyme that catalyzes the transfer of a methyl group to DNA. Examples of DNA methyltransferases include but are not limited to: DNMT1, DNMT3A, and DNMT3B (FIG. 2). In some embodiments, an epigenetic modulator of FMR1 is a DNA methyltransferase inhibitor. Examples of small molecule inhibitors of DNA methyltransferases are shown in Table 1.

As used herein, the term "histone methyltransferase" refers to an enzyme that catalyzes the transfer of a methyl group to a histone protein. Examples of histone methyltransferases include, but are not limited to, EZH2, SETDB1, EHMT1/GLP, EHMT2/G9a, SUV39H1, SUV420H1, and SUV420H2 (FIG. 2). In some embodiments, an epigenetic modulator of FMR1 is a histone methyltransferase inhibitor. Examples of small molecule inhibitors of histone methyltransferases are shown in Table 1.

As used herein, the term "histone ubiquitin ligase" refers to an enzyme that recruits an E2 ubiquitin-conjugating enzyme that has been loaded with ubiquitin, recognizes a protein substrate (e.g., a histone protein), and assists or directly catalyzes the transfer of ubiquitin from the E2 to the protein substrate (e.g., histone protein). In some embodiments, the disclosure relates to inhibitors of E3 ubiquitin ligase enzymes. E3 ubiquitin ligases are generally split into four families (HECT, RING-finger, U-box and PHD-finger). In some embodiments, the disclosure relates to inhibitors of RING ubiquitin ligase enzymes. In some embodiments, the disclosure relates to inhibitors of histone 2A (H2A) ubiquitin ligase enzymes (e.g., RING1B/RNF2). Examples of small molecule inhibitors of ubiquitin ligase enzymes are shown in Table 1.

a histone deacetylase. Examples of small molecule inhibitors of histone deacetylases are shown in Table 1.

In some embodiments, an epigenetic modulator of FMR1 is a selective inhibitor. As used herein, a "selective inhibitor" or an inhibitor that is said to "selectively inhibit" refers to an inhibitor that preferentially inhibits activity or expression of a target molecule of a particular class compared with other molecules of the class. In some embodiments, a selective inhibitor of a target molecule of a particular class has half maximal inhibitory concentration (IC50) relative to the target molecule that is at least 2-fold, at least 4-fold, at least 8-fold, at least 10-fold, at least 20-fold, at least 30-fold, at least 40-fold, or at least 50-fold lower than the IC50 relative to one or more other members of the class. A selective inhibitor can be an inhibitor of: a methyltransferase (e.g., DNA methyltransferase or histone methyltransferase), a histone ubiquitin ligase (e.g., a ubiquitin ligase that ubiquitinates histone H2A), a histone deacetylase (e.g., HDAC, SIRT5), or a histone demethylase (e.g., KDM5D).

In some embodiments, a selective inhibitor selectively inhibits a DNA methyltransferase. In some embodiments, a

TABLE 1

| Chromatin Modifier | Small Molecule Inhibitors (epigenetic modulators) |
|---|---|
| DNMT1 | Procainamide; SGI-1027 (and analogs); RG108; CBC12; 5-azacytidine; 5-aza-2'-deoxycytidine (5-Aza-CdR); 5-Azacytidine (5-Aza-CR); 6- dihydro-5-azacytidine; zebularine; 5-fluoro-2'-deoxycytidine; NPEOC-DAC; SI 10; hydralazine; RG108; SGI-1027; decitabine; zebularine; 5F-2'-deoxycytidine; hydralazine; EGCG; parthenolide; NSC14778; RG108-1; mahanine; ATA; doxorubicin; amsacrine; actinomycin; mitoxantrone; tetrahydrouridine (THU); NPEOC-DAC; S110; miR29a; valproic acid (VPA); EFOG; psammaplin A; MG98 |
| EZH2 | S-adenosyl-L-homocysteine(SAH) hydrolase inhibitors; S-adenosyl-1-methionine (SAM)-competitive inhibitors; 3-deazaneplanocin A (DZNep); E-7438 (EPZ-6438); EPZ-005687; GSK126; GSK343; GSK926; GSK2816126; UNC-1999; EI1; sinefungin; GSK-A. |
| SUV39H1 | Chaetocin; DBC1; Verticillin A |
| RING1B/RNF2 | PRT4165 |
| HDAC5 | LMK 235; MC1568; Quisinostat; CUDC-101; Pracinostat; TMP269; CUDC-907; miR-2861; SAHA; Tacedinaline; Belinostat; Scriptaid; Gavinostat; SB939; LBH589; PXD101; AR-42; LAQ-824; LBH-589; butyrate; phenylbutyrate; Sodium butyrate; Sodium 4-Phenylbutyrate; valproic acid; CBHA; ITF2357; PCI-24781; FK-228; AN-9; MS-275; MC 1568; KD 5170; M 344; NCH 51; NSC 3852; Pyroxamide; SBHA; Romidepsin. |
| HDAC10 | Bufexamac; trichostatin A; bufexamac; PI3K, PCI-24781, JNJ-26481585; SAHA; Tacedinaline; Belinostat; Scriptaid; Gavinostat; SB939; LBH589; MGCD0103; PXD101; AR-42; LAQ-824; LBH-589; butyrate; phenylbutyrate; Sodium butyrate; Sodium 4-Phenylbutyrate; valproic acid; m-carboxycinnamic acid bishydroxamic acid CBHA; ITF2357; PCI-24781; FK-228; AN-9; MS-275; MC 1568; KD 5170; M 344; NCH 51; NSC 3852; Pyroxamide; SBHA; Romidepsin; ABHA. |
| SIRT5 | Suramin sodium, cambinol; H3K9TSu (thiosuccinyl peptides); Thiobarbiturates; GW5074; thiomalonyl peptides; Nicotinamide |
| KDM5D | 2,4-PDCA; catechols; PBIT; NOG; quercetin; disulfram; ebselen; SAHA; |
| KDM5C | GSK J1/Chemical name: N-[2-(2-Pyridinyl)-6-(1,2,4,5-tetrahydro-3H-3-benzazepin-3-yl)-4-pyrimidinyl]-β-alanine; GSK J4/Chemical name: N-[2-(2-Pyridinyl)-6-(1,2,4,5-tetrahydro-3H-3-benzazepin-3-yl)-4-pyrimidinyl]-β-alanine ethyl ester; TC-E 5002/Chemical name: N-(9-Cyclopropyl-1-oxononyl)-N-hydroxy-β-alanine |

As used herein, the term "histone acetyltransferase" refers to an enzyme that catalyzes transfer of an acetyl group to conserved lysine residues on histone proteins. Generally, histone acetylation functions as an active epigenetic marker. In some aspects, the invention relates to the discovery that histone acetylation is reduced in silenced FMR1. Thus, in some aspects, the invention relates to epigenetic modulators of FMR1 that inhibit inhibitors of histone acetylation. For example, histone deacetylases remove acetyl groups from histone proteins. Examples of histone deacetylases include, but are not limited to, histone deacetylases 1-10 (HDAC1-HDAC10), sirtuins 1-7 (SIRT1-7), and Lysine-specific demethylases 5A-5D (KDM5A-D) (FIG. 2). In some embodiments, an epigenetic modulator of FMR1 is an inhibitor of selective inhibitor of DNMT1, which is a DNA methyltransferase, has half maximal inhibitory concentration (IC50) relative to DNMT1 that is at least 2-fold, at least 4-fold, at least 8-fold, at least 10-fold, at least 20-fold, at least 30-fold, at least 40-fold, or at least 50-fold lower than the IC50 relative to one or more other DNA methyltransferases. However, in some embodiments, an inhibitor of a DNA methyltransferase is not selective for any one particular member of the class but rather targets more than one member, e.g., functions as a pan inhibitor of DNA methyltransferases.

In some embodiments, a selective inhibitor selectively inhibits a histone methyltransferase. In some embodiments, the histone methyltransferase is SUV39H1. In some embodiments, the histone methyltransferase is EPZ2. In some embodiments, a selective inhibitor of SUV39H1 has half maximal inhibitory concentration (IC50) relative to SUV39H1 that is at least 2-fold, at least 4-fold, at least 8-fold, at least 10-fold, at least 20-fold, at least 30-fold, at least 40-fold, or at least 50-fold lower than the IC50 relative to one or more other histone methyltransferases. In some embodiments, a selective inhibitor of EPZ2 has half maximal inhibitory concentration (IC50) relative to EPZ2 that is at least 2-fold, at least 4-fold, at least 8-fold, at least 10-fold, at least 20-fold, at least 30-fold, at least 40-fold, or at least 50-fold lower than the IC50 relative to one or more other histone methyltransferases. However, in some embodiments, an inhibitor of a histone methyltransferase is not selective for any one particular member of the class but rather targets more than one member, e.g., functions as a pan inhibitor of histone methyltransferases.

In some embodiments, a selective inhibitor selectively inhibits a histone ubiquitin ligase. In some embodiments, a selective inhibitor of RING1B/RNF2, which is a histone ubiquitin ligase, has half maximal inhibitory concentration (IC50) relative to RING1B/RNF2 that is at least 2-fold, at least 4-fold, at least 8-fold, at least 10-fold, at least 20-fold, at least 30-fold, at least 40-fold, or at least 50-fold lower than the IC50 relative to one or more histone ubiquitin ligases. However, in some embodiments, an inhibitor of a histone ubiquitin ligase is not selective for any one particular member of the class but rather targets more than one member, e.g., functions as a pan inhibitor of histone ubiquitin ligases.

In some embodiments, a selective inhibitor selectively inhibits a histone deacetylase (e.g., HDAC or SIRT5). In some embodiments, a selective inhibitor of HDAC5, which is a histone deacetylase, has half maximal inhibitory concentration (IC50) relative to HDAC5 that is at least 2-fold, at least 4-fold, at least 8-fold, at least 10-fold, at least 20-fold, at least 30-fold, at least 40-fold, or at least 50-fold lower than the IC50 relative to one or more histone deacetylases. In some embodiments, a selective inhibitor of HDAC10, which is a histone deacetylase, has half maximal inhibitory concentration (IC50) relative to HDAC10 that is at least 2-fold, at least 4-fold, at least 8-fold, at least 10-fold, at least 20-fold, at least 30-fold, at least 40-fold, or at least 50-fold lower than the IC50 relative to one or more histone deacetylases. In some embodiments, a selective inhibitor of SIRT5, which is a histone deacetylase, has half maximal inhibitory concentration (IC50) relative to SIRT5 that is at least 2-fold, at least 4-fold, at least 8-fold, at least 10-fold, at least 20-fold, at least 30-fold, at least 40-fold, or at least 50-fold lower than the IC50 relative to one or more histone deacetylases. However, in some embodiments, an inhibitor of a histone deacetylase is not selective for any one particular member of the class but rather targets more than one member, e.g., functions as a pan inhibitor of histone deacetylases.

In some embodiments, a selective inhibitor selectively inhibits a histone demethylase. In some embodiments, a selective inhibitor of KDM5D or KDM5C, which is a histone demethylase, has half maximal inhibitory concentration (IC50) relative to KDM5D or KDM5C that is at least 2-fold, at least 4-fold, at least 8-fold, at least 10-fold, at least 20-fold, at least 30-fold, at least 40-fold, or at least 50-fold lower than the IC50 relative to one or more other histone demethylases. However, in some embodiments, an inhibitor of a histone demethylase is not selective for any one particular member of the class but rather targets more than one member, e.g., functions as a pan inhibitor of histone demethylases.

In some embodiments, an epigenetic modulator of FMR1 is an interfering RNA. Examples of interfering RNA include, but are not limited to double stranded RNA (dsRNA), siRNA, shRNA, miRNA, and antisense oligonucleotide (ASO). Inhibitory oligonucleotides may interfere with gene expression, transcription and/or translation. Generally, inhibitory oligonucleotides bind to a target polynucleotide via a region of complementarity. For example, binding of inhibitory oligonucleotide to a target polynucleotide can trigger RNAi pathway-mediated degradation of the target polynucleotide (in the case of dsRNA, siRNA, shRNA, etc.), or can block the translational machinery (e.g., antisense oligonucleotides). Inhibitory oligonucleotides can be single-stranded or double-stranded. In some embodiments, inhibitory oligonucleotides are DNA or RNA. In some embodiments, the inhibitory oligonucleotide is selected from the group consisting of: antisense oligonucleotide, siRNA, shRNA and miRNA. In some embodiments, inhibitory oligonucleotides are modified nucleic acids.

The term "nucleotide analog" or "altered nucleotide" or "modified nucleotide" refers to a non-standard nucleotide, including non-naturally occurring ribonucleotides or deoxyribonucleotides. In some embodiments, nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguano sine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438. A locked nucleic acid (LNA), often referred to as inaccessible RNA, is a modified RNA nucleotide. The ribose moiety of an LNA nucleotide is modified with an extra bridge connecting the T oxygen and 4' carbon.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro. In some embodiments, the inhibitory oligonucleotide is a modified inhibitory oligonucleotide. In some embodiments, the modified inhibitory oligonucleotide comprises a locked nucleic acid (LNA), phosphorothioate backbone, and/or a 2'-OMe modification. Table 2 below provides examples of interfering RNA that are epigenetic modulators of FMR1.

TABLE 2

Examples of Interfering RNA Epigenetic Modulators of FMR1

| Gene | shRNA sequences (mature antisense guide strands) | SEQ ID NO: |
|---|---|---|
| DNMT1 | ATCCATCAGAATGTATTCGGC | 1 |
|  | TTGATGTCAGTCTCATTGGGC | 2 |
| EZH2 | GCAGCTGGTGAGAAGGCAATA | 3 |
|  | TTTGGTCCCAATTAACCTAGC | 4 |
| SUV39H1 | TTGTGGCAAAGAAAGCGATGC | 5 |
|  | AATAGGCCATGAATCCCAACG | 6 |
| RING1B/RNF2 | TTTGGTCCGTTTGTTACTAGG | 7 |
|  | TTCTAAAGCTAACCTCACAGC | 8 |
| HDAC5 | TTAAAGGTGCTAATAACAGTC | 9 |
|  | ATCTCGATGACTTTCTCTAGC | 10 |
| HDAC10 | TGCGGTGTCATTTCTGCGGTG | 11 |
|  | TAGCCCGTGTTTCTGCTTGGC | 12 |
| SIRT5 | AAACCTGAATCTGTTCGTAGC | 13 |
|  | AAATCTGGTTTCGTGTGGACG | 14 |
| KDM5D | AATGCGTTCGTAATGTGATCG | 15 |
|  | AACAGACTGATCTAGCACTGG | 16 |
| KDM5C | AAACAATGCGTTCGTAGTGGG | 17 |
|  | TTAGGTGCCGTTTACTGTCAC | 18 |

Methods of Treatment

In some aspects, the disclosure provides methods for treating a subject having a FMR1-inactivation-associated disorder. For example, transcriptional inactivation of the FMR1 gene may lead to FXS in a subject. As used herein, a "subject" is interchangeable with a "subject in need thereof", both of which may refer to a subject having a FMR1-inactivation-associated disorder, or a subject having an increased risk of developing such a disorder relative to the population at large. A subject in need thereof may be a subject having an inactive FMR1 gene. A subject can be a human, non-human primate, rat, mouse, cat, dog, or other mammal. In some embodiments, the FMR1-inactivation-associated disorder is fragile X syndrome, fragile X-associated tremor/ataxia syndrome, premature ovarian aging, or polycystic ovarian syndrome.

As used herein, the terms "treatment", "treating", and "therapy" refer to therapeutic treatment and prophylactic or preventative manipulations. The terms further include ameliorating existing symptoms, preventing additional symptoms, ameliorating or preventing the underlying causes of symptoms, preventing or reversing causes of symptoms, for example, symptoms associated with a FMR1-inactivation-associated disorder. Thus, the terms denote that a beneficial result has been conferred on a subject with a disorder (e.g., a FMR1-inactivation-associated disorder), or with the potential to develop such a disorder. Furthermore, the term "treatment" is defined as the application or administration of an agent (e.g., therapeutic agent or a therapeutic composition) to a subject, or an isolated tissue or cell line from a subject, who may have a disease, a symptom of disease or a predisposition toward a disease, with the purpose to cure, heal, alleviate, relieve, alter, remedy, ameliorate, improve or affect the disease, the symptoms of disease or the predisposition toward disease.

Therapeutic agents or therapeutic compositions may include a compound in a pharmaceutically acceptable form that prevents and/or reduces the symptoms of a particular disease (e.g., a FMR1-inactivation-associated disorder). For example a therapeutic composition may be a pharmaceutical composition that prevents and/or reduces the symptoms of a FMR1-inactivation-associated disorder. It is contemplated that the therapeutic composition of the present invention will be provided in any suitable form. The form of the therapeutic composition will depend on a number of factors, including the mode of administration as described herein. The therapeutic composition may contain diluents, adjuvants and excipients, among other ingredients as described herein.

In some aspects, the disclosure provides a method for reactivating a transcriptionally inactive FMR1 gene in a cell, the method comprising: contacting the cell with an effective amount of an epigenetic modulator of FMR1, wherein the epigenetic modulator reactivates FMR1 in the cell. In some embodiments, the cell is in vitro.

The cell contacted with the effective amount of an epigenetic modulator of FMR1 can be any cell that has a transcriptionally inactive FMR1 gene. For example, the cell can be a brain cell, a testicular cell, an ovarian cell, a spleen cell, a thymus cell, or an ocular cell. In some embodiments, the cell is an induced pluripotent stem cell (iPSC). A cell having a transcriptionally inactive FMR1 gene generally bears one or more epigenetic marks indicative of having a transcriptionally inactive (e.g., epigenetically silenced) FMR1 gene. Epigenetic marks can be activating marks, repressive marks, or activating marks and repressive marks. Examples of epigenetic repressive marks associated with transcriptionally inactive FMR1 gene include DNA methylation (DNAme), histone H3 lysine 27 trimethylation (H3K27me3), histone H3 lysine 9 trimethylation (H3K9me3), histone 4 lysine 20 trimethylation (H4K20me3), histone H2A ubiquitination (H2Aub). Examples of epigenetic activating marks that are found at reduced levels on transcriptionally inactive FMR1 include histone H2a acetylation, histone H2B acetylation, histone H3 acetylation, histone H4 acetylation, and histone H3 lysine 4 trimethylation (H3K4me3).

A cell having a transcriptionally inactive FMR1 gene can also comprise an expansion of a polymorphic CGG repeat within the 5'UTR of the FMR1 gene. The number of repeats in the expansion can vary. In some embodiments, the number of CGG repeats in the expansion ranges from about 55 to about 500 repeats. In some embodiments, the number of CGG repeats ranges from about 55 repeats to about 200 repeats. In some embodiments, the number of CGG repeats ranges from about 100 to about 500 repeats. In some embodiments, the number of CGG repeats is greater than 200 repeats. In some embodiments, the number of CGG repeats is greater than 500 repeats.

Pharmaceutical Compositions

In some aspects, the disclosure relates to pharmaceutical compositions comprising an epigenetic modulator of FMR1. In some embodiments, the composition comprises an epigenetic modulator of FMR1 and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below. The active ingredients may be admixed or compounded with any conventional, pharmaceutically acceptable carrier or excipient. The compositions may be sterile.

Typically, pharmaceutical compositions are formulated for delivering an effective amount of an agent (e.g., an epigenetic modulator of FMR1). In general, an "effective amount" of an active agent refers to an amount sufficient to elicit the desired biological response (e.g., reactivation of the inactive FMR1 gene). An effective amount of an agent may vary depending on such factors as the desired biological endpoint, the pharmacokinetics of the compound, the disease being treated (e.g., a FMR1-inactivation-associated disorder), the mode of administration, and the patient.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, REMINGTON'S PHARMACEUTICAL SCIENCES, 18th Ed. (1990).

It will be understood by those skilled in the art that any mode of administration, vehicle or carrier conventionally employed and which is inert with respect to the active agent may be utilized for preparing and administering the pharmaceutical compositions of the present disclosure. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the disclosure, will experience no difficulty in determining suitable and appropriate vehicles, excipients and carriers or in compounding the active ingredients therewith to form the pharmaceutical compositions of the disclosure.

An effective amount, also referred to as a therapeutically effective amount, of a compound (for example, an antisense nucleic acid (e.g., oligonucleotide) or small molecule epigenetic modulator of FMR1) is an amount sufficient to ameliorate at least one adverse effect associated with inactivation (e.g., transcriptional inactivation), or reduced expression, of the gene in a cell or in an individual in need of such modulation. In some embodiments, an effective amount is an amount sufficient to reactivate FMR1 gene in a cell or in an individual in need of FMR1 reactivation. The therapeutically effective amount to be included in pharmaceutical compositions depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg. One of ordinary skill in the art would be able to determine empirically an appropriate therapeutically effective amount.

Combined with the teachings provided herein, by choosing among the various active compounds and weighing factors such as potency, relative bioavailability, patient body weight, severity of adverse side-effects and selected mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered, the size of the subject, or the severity of the disease or condition. One of ordinary skill in the art can empirically determine the effective amount of a particular nucleic acid and/or other therapeutic agent without necessitating undue experimentation.

In some cases, compounds of the disclosure are prepared in a colloidal dispersion system. Colloidal dispersion systems include lipid-based systems including oil-in-water emulsions, micelles, mixed micelles, and liposomes. In some embodiments, a colloidal system of the disclosure is a liposome. Liposomes are artificial membrane vessels which are useful as a delivery vector in vivo or in vitro. It has been shown that large unilamellar vesicles (LUVs), which range in size from 0.2-4.0 μm can encapsulate large macromolecules. RNA, DNA and intact virions can be encapsulated within the aqueous interior and be delivered to cells in a biologically active form. Fraley et al. (1981) Trends Biochem Sci 6:77.

Liposomes may be targeted to a particular tissue by coupling the liposome to a specific ligand such as a monoclonal antibody, sugar, glycolipid, or protein. Ligands which may be useful for targeting a liposome to, for example, an smooth muscle cell include, but are not limited to: intact or fragments of molecules which interact with smooth muscle cell specific receptors and molecules, such as antibodies, which interact with the cell surface markers of cancer cells. Such ligands may easily be identified by binding assays well known to those of skill in the art. In still other embodiments, the liposome may be targeted to a tissue by coupling it to an antibody known in the art.

Lipid formulations for transfection are commercially available from QIAGEN, for example, as EFFECTENE™ (a non-liposomal lipid with a special DNA condensing enhancer) and SUPERFECT™ (a novel acting dendrimeric technology).

Liposomes are commercially available from Gibco BRL, for example, as LIPOFECTIN™ and LIPOFECTACE™, which are formed of cationic lipids such as N-[1-(2, 3 dioleyloxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) Trends Biotechnol 3:235-241.

Certain cationic lipids, including in particular N-[1-(2, 3 dioleoyloxy)-propyl]-N,N,N-trimethylammonium methylsulfate (DOTAP), may be advantageous when combined with the epigenetic modulators of FMR1 (e.g., interfering RNA) of the disclosure.

In some aspects of the disclosure, the use of compaction agents may also be desirable. Compaction agents also can be used alone, or in combination with, a biological or chemical/physical vector. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, e.g., to deliver an epigenetic modulator of FMR1 in a form that is more efficiently taken up by the cell or, in combination with one or more of the above-described carriers.

Other exemplary compositions that can be used to facilitate uptake of an epigenetic modulator of FMR1 include calcium phosphate and other chemical mediators of intracellular transport, microinjection compositions, electroporation and homologous recombination compositions (e.g., for integrating a nucleic acid into a preselected location within the target cell chromosome).

The compounds may be administered alone (e.g., in saline or buffer) or using any delivery vehicle known in the art. For instance the following delivery vehicles have been described: cochleates; Emulsomes; ISCOMs; liposomes; live bacterial vectors (e.g., *Salmonella, Escherichia coli, Bacillus* Calmette-Guérin, *Shigella, Lactobacillus*); live viral vectors (e.g., Vaccinia, adenovirus, Herpes Simplex); microspheres; nucleic acid vaccines; polymers (e.g., carboxymethylcellulose, chitosan); polymer rings; proteosomes; sodium fluoride; transgenic plants; virosomes; and, virus-like particles.

The formulations of the disclosure are administered in pharmaceutically acceptable solutions, which may routinely contain pharmaceutically acceptable concentrations of salt, buffering agents, preservatives, compatible carriers, adjuvants, and optionally other therapeutic ingredients.

The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present disclosure, and with each other, in a manner such that there is no interaction which would substantially impair the desired pharmaceutical efficiency.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In addition to the formulations described herein, the compounds may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) Science 249:1527-1533, which is incorporated herein by reference.

The compounds may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Modes of Administration

The pharmaceutical compositions of the present disclosure preferably contain a pharmaceutically acceptable carrier or excipient suitable for rendering the compound or mixture administrable orally as a tablet, capsule or pill, or parenterally, intravenously, intradermally, intramuscularly or subcutaneously, or transdermally.

In some embodiments, a therapeutically effective amount of an epigenetic modulator of FMR1 is delivered to a target tissue or a target cell. Generally, FMR1 is widely expressed in human embryos. Thus, in some embodiments, a therapeutically effective amount of an epigenetic modulator of FMR1 is delivered to the brain, testes, ovaries, esophagus, epithelium, thymus, eye and/or spleen of a subject. In some embodiments, an effective amount of epigenetic modulator of FMR1 is delivered to the central nervous system (CNS) of a subject. In some embodiments, an effective amount of epigenetic modulator of FMR1 is delivered to a neuronal cell of a subject, for example a differentiated neuronal cell. Examples of differentiated neuronal cells include, but are not limited to, motor neurons, sensory neurons, peripheral neurons, interneurons, Purkinje cells, Granule cells, tripolar neurons, pyramidal cells, Chandelier cells, spindle neurons, stellate cells, basket cells, ganglion cells, and hair cells.

The pharmaceutical compositions containing an epigenetic modulator of FMR1 and/or other compounds can be administered by any suitable route for administering medications. A variety of administration routes are available. The particular mode selected will depend, of course, upon the particular agent or agents selected, the particular condition being treated, and the dosage required for therapeutic efficacy. The methods of this disclosure, generally speaking, may be practiced using any mode of administration that is medically acceptable, meaning any mode that produces therapeutic effect without causing clinically unacceptable adverse effects. Various modes of administration are discussed herein. For use in therapy, an effective amount of the epigenetic modulator of FMR1 and/or other therapeutic agent can be administered to a subject by any mode that delivers the agent to the desired surface, e.g., mucosal, systemic.

Administering the pharmaceutical composition of the present disclosure may be accomplished by any means known to the skilled artisan. Routes of administration include but are not limited to oral, parenteral, intravenous, intramuscular, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In some embodiments, an inhibitory oligonucleotide (e.g., interfering RNA) can be delivered to the cells via an expression vector engineered to express the inhibitor oligonucleotide. An expression vector is one into which a desired sequence may be inserted, e.g., by restriction and ligation, such that it is operably joined to regulatory sequences and may be expressed as an RNA transcript. An expression vector typically contains an insert that is a coding sequence for a protein or for a inhibitory oligonucleotide such as an shRNA, a miRNA, or an miRNA. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays or fluorescent proteins, etc.

As used herein, a coding sequence (e.g., protein coding sequence, miRNA sequence, shRNA sequence) and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. It will be appreciated that a coding sequence may encode an miRNA, shRNA or miRNA.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences will include a promoter region that includes a promoter sequence for tran-scriptional control of the operably joined gene. Regulatory sequences may also include enhancer sequences or upstream activator sequences as desired. The vectors of the disclosure may optionally include 5' leader or signal sequences.

In some embodiments, a virus vector for delivering a nucleic acid molecule is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses, a modified retrovirus, a nonreplicating retrovirus, a replication defective Semliki Forest virus, canarypox virus and highly attenuated vaccinia virus derivative, non-replicative vaccinia virus, replicative vaccinia virus, Venzuelan equine encephalitis virus, Sindbis virus, lentiviral vectors and Ty virus-like particle. Another virus useful for certain applications is the adeno-associated virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other useful viral vectors are based on non-cytopathic eukaryotic viruses in which non-essential genes have been replaced with the gene of interest. Non-cytopathic viruses include certain retroviruses, the life cycle of which involves reverse transcription of genomic viral RNA into DNA with subsequent proviral integration into host cellular DNA. In general, the retroviruses are replication-deficient (e.g., capable of directing synthesis of the desired transcripts, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, New Jersey (1991).

Various techniques may be employed for introducing nucleic acid molecules of the disclosure into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. Other examples include: N-TER™ Nanoparticle Transfection System by Sigma-Aldrich, FectoFly™ transfection reagents for insect cells by Polyplus Transfection, Polyethylenimine "Max" by Polysciences, Inc., Unique, Non-Viral Transfection Tool by Cosmo Bio Co., Ltd., Lipofectamine™ LTX Transfection Reagent by Invitrogen, SatisFection™ Transfection Reagent by Stratagene, Lipofectamine™ Transfection Reagent by Invitrogen, FuGENE® HD Transfection Reagent by Roche Applied Science, GMP compliant in vivo-jetPEI™ transfection reagent by Polyplus Transfection, and Insect GeneJuice® Transfection Reagent by Novagen.

Screening Methods

In some aspects, the disclosure relates to methods of identifying agents that function as epigenetic modulators of FMR1. Accordingly, in some embodiments, the disclosure provides a method for identifying epigenetic modulators of FMR1, the method comprising: contacting a cell comprising an inactivated FMR1 gene with a candidate agent; detecting expression level FMR1 in the cell; and, identifying the candidate agent as an epigenetic modulator of FMR1 when the expression level of FMR1 increases relative to a control cell after contact with the candidate agent.

As used herein, the term "candidate agent" refers to any agent (e.g., compound) wherein the characterization of the compound's ability to reactivate silenced FMR1 gene is desirable. Exemplary candidate agents include, but are not limited to small molecules, antibodies, antibody conjugates, peptides, proteins, and/or antisense molecules (e.g., interfering RNAs). In some embodiments, methods described by the disclosure are useful for screening large libraries of candidate compounds (e.g., compound libraries) to identify new epigenetic modulators of FMR1. In some embodiments, compound libraries consist of candidate agents specific for a particular target, for example an activating mark, a repressive mark, or a ubiquitin ligase. Compound libraries may also consist of candidate agents that are specific for a particular protein target, such as a DNA methyltransferase, a histone methyltransferase, a ubiquitin ligase, and/or a histone acetyltransferase. In some embodiments, candidate agents are inhibitors of a DNA methyltransferase, a histone methyltransferase, a ubiquitin ligase, and/or a histone acetyltransferase.

The skilled artisan recognizes several methods for contacting the cell having an inactivated FMR1 gene with the candidate compound. For example, automated liquid handling systems are generally utilized for high throughput drug screening. Automated liquid handling systems utilize arrays of liquid dispensing vessels, controlled by a robotic arm, to distribute fixed volumes of liquid to the wells of an assay plate. Generally, the arrays comprise 96, 384 or 1536 liquid dispensing tips. Non-limiting examples of automated liquid handling systems include digital dispensers (e.g., HP D300 Digital Dispenser) and pinning machines (e.g., MULTI-BLOT™ Replicator System, CyBio, Perkin Elmer Janus). Non-automated methods are also contemplated by the disclosure, and include but are not limited to a manual digital repeat multichannel pipette.

In some embodiments, screening methods described by the disclosure are carried out in a high throughput mode. In some embodiments, high-throughput screening is carried out in a multi-well cell culture plate. In some embodiments, the multi-well plate is plastic or glass. In some embodiments, the multi-well plate comprises an array of 6, 24, 96, 384 or 1536 wells. However, the skilled artisan recognizes that multi-well plates may be constructed into a variety of other acceptable configurations, such as a multi-well plate having a number of wells that is a multiple of 6, 24, 96, 384 or 1536. For example, in some embodiments, the multi-well plate comprises an array of 3072 wells (which is a multiple of 1536).

The expression level FMR1 in the cell can be measured by any suitable means known in the art. For example, expression level of FMR1 in a cell can be measured by a hybridization-based method. Examples of hybridization-based assays include reverse transcription polymerase chain reaction (RT-PCR), quantitative RT-PCR (qRT-PCR), Northern blot, and Southern blot. In some embodiments, the expression level FMR1 in the cell is measured by a protein-based method. Examples of protein-based assays include, but are not limited to, Western blot, Bradford assay, Lowry protein assay, and spectroscopic methods (e.g., mass spectrometry, high pressure liquid chromatography, etc.). In some embodiments, expression level FMR1 in the cell is determined by a cell-based method. Examples of cell-based assays include immunofluorescence, flow cytometry, fluorescent activated cell sorting (FACS), magnetic-activated cell sorting (MACS). In some embodiments, cells are modified such that FMR1 activation is operably linked to expression of a resistance gene, and thus reactivation of silenced FMR1 allows growth and selection of cells in the presence of a selection media (See FIG. 5). In some embodiments, cells are modified such that FMR1 activation is operably linked to expression of a fluorescent protein, and thus reactivation of silenced FMR1 allows for expression of a fluorescent protein that can be detected by immunofluorescence or FACS. Additional methods of quantifying expression level FMR1 in the cell will be readily apparent to those skilled in the art.

A candidate compound can be identified as an epigenetic modulator of FMR1 if the amount of FMR1 expressed in the presence of the candidate compound is more than the amount expressed in the absence of candidate compound. The amount of FMR1 expressed in the presence of an epigenetic modulator of FMR1 can range from about 2-fold more to about 500-fold more, 5-fold more to about 250-fold more, 10-fold more to about 150-fold more, or about 20-fold more to about 100-fold more, than the amount of FMR1 expressed in the absence of the epigenetic modulator of FMR1. In some embodiments, the amount of FMR1 expressed in the presence of an epigenetic modulator of FMR1 can range from about 1% to about 1000% more, about 10% to about 500% more, about 20% to about 250% more, about 50% to about 500% more, about 100% to about 750% more than the amount of FMR1 expressed in the absence of the epigenetic modulator of FMR1. In some embodiments, FMR1 is expressed in the presence of an epigenetic modulator of FMR1 and is not expressed (e.g., transcriptionally inactive or silenced) in the absence of an epigenetic modulator of FMR1.

EXAMPLES

Example 1

Factors responsible for depositing repressive marks or for removing activating marks are potential targets to reactivate the epigenetically silenced FMR1 gene (FIG. 2). The following table (Table 3) is a non-comprehensive list of factors responsible for depositing or removing the epigenetic marks on the silenced FMR1 gene.

TABLE 3

Potential Chromatin Modifier Targets for Epigenetic Modulators of FMR1

| Epigenetic mark | Potential target(s) |
|---|---|
| DNAme | DNMT1, DNMT3A, DNMT3B |
| H3K27me3 | EZH2 |
| H3K9me3 | SETDB1, EHMT1/GLP, EHMT2/G9a, SUV39H1 |
| H4K20me3 | SUV420H1, SUV420H2 |
| H2Aub | RING1B/RNF2 |
| H2A/2B/3/4ac | HDAC1-10, SIRT1-7 |
| H3K4me3 | KDM5A-D |

Figure 3:
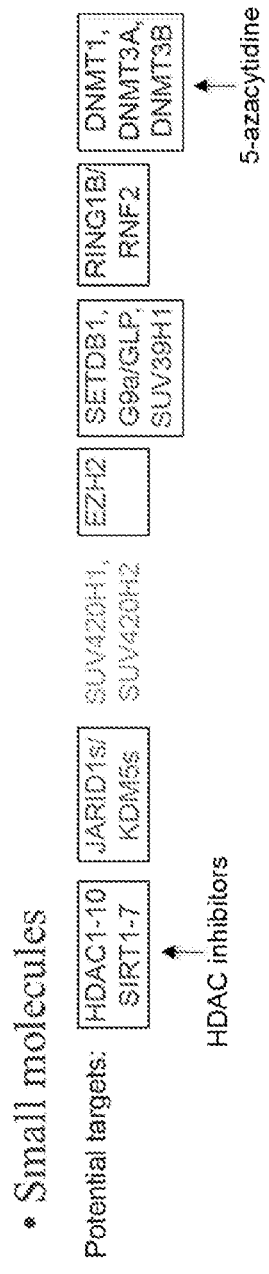
FIG. 3 shows a schematic of a candidate-based screen of inhibitors of chromatin modifiers of silenced FMR1 gene.

All of the factors required for depositing or removing the epigenetic marks mentioned in the above table have been systematically knocked down using short hairpin RNAs (shRNAs) (FIG. 3). These experiments were performed in induced pluripotent stem cells (iPSCs) derived from an FXS patient. FXS iPSCs harbor a repressed FMR1 gene, and therefore serve as a useful model system for studying disease mechanisms and for drug screening approaches.

Figure 4:
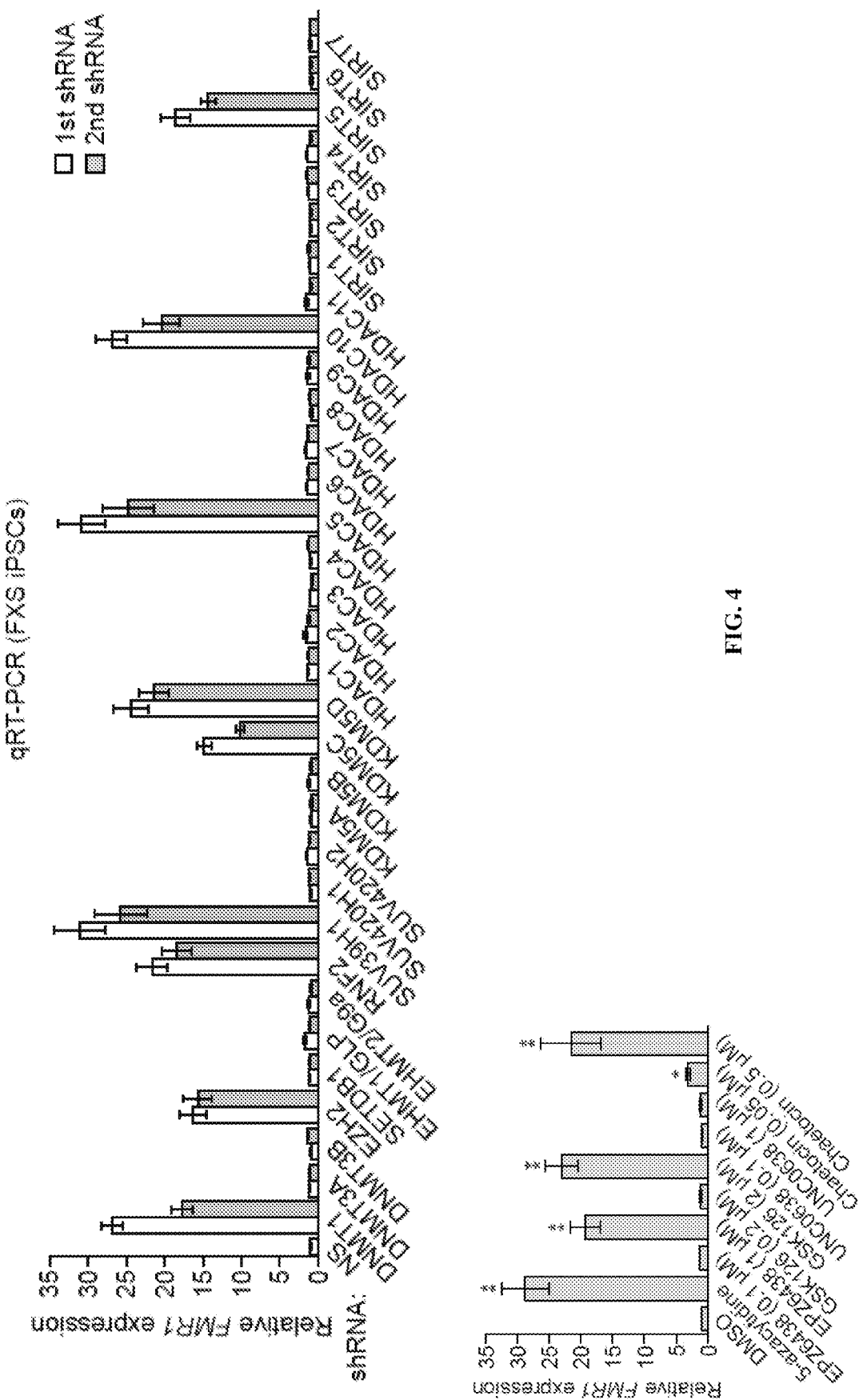
FIG. 4 shows identification of shRNAs and small molecule inhibitors that reactivate FMR1 expression in FXS iPSCs. The top panel shows qRT-PCR analysis monitoring expression of FMR1 in FXS iPSCs treated with two independent shRNAs directed against a chromatin modifier, as indicated. FMR1 expression was normalized to that obtained upon expression of a control non-silencing (NS) shRNA, which was set to 1. The bottom panel shows qRT-PCR analysis monitoring expression of FMR1 in iPSCs treated with EPZ6438 or GSK126 (inhibitors of EZH2), UNC0638 (an EHMT2/G9a inhibitor), and chaetocin (SUV39H1 inhibitor). FMR1 expression was normalized to that obtained upon treatment with the vehicle DMSO, which was set to 1. *P<0.05, **P<0.01.

Using this directed approach, nine chromatin modifiers were identified that, when knocked down, activate expression of the FMR1 gene in iPSC cells. The nine modifiers are: DNMT1, EZH2, SUV39H1, RING1B/RNF2, HDAC5, HDAC10, SIRT5, KDM5C and KDM5D (FIG. 4, top). For many of these factors (all except SUV420H1 and SUV420H2), small molecule inhibitors are available (Table 1). Therefore whether small molecule inhibitors can, like RNAi knockdown, de-repress the FMR1 gene was tested. Four compounds, EZH2 inhibitors EPZ6438 (Cayman Chemical) and GSK126 (Apexbio Technology), the G9a (also known as EHMT2) inhibitor UNC0638 (Sigma-Aldrich), and the SUV39H1 inhibitor chaetocin (Tocris Bioscience) were tested. In addition, the DNMT inhibitor 5-azacytidine was analyzed as a positive control. The 5-azacytidine, EPZ6438, GSK126 and chaetocin reactivate FMR1, whereas UNC0638 does not (FIG. 4, bottom), consistent with the results of shRNA-mediated knockdown of the cognate genes (see FIG. 4, top). This is an important result because it was previously suggested that G9a was the H3K9 methyltransferase involved in R-loop-initiated epigenetic silencing.]

De-repressing the FMR1 gene represents a novel therapeutic approach by which to reverse FXS symptoms. A number of factors that are targets for discovery of biological or small molecule inhibitors that will reactivate the silenced FMR1 gene have been identified. In addition, for a previously described small molecule inhibitor, chaetocin, a novel biological role in de-repressing expression of the FMR1 gene was discovered.

Example 2

Figure 5:
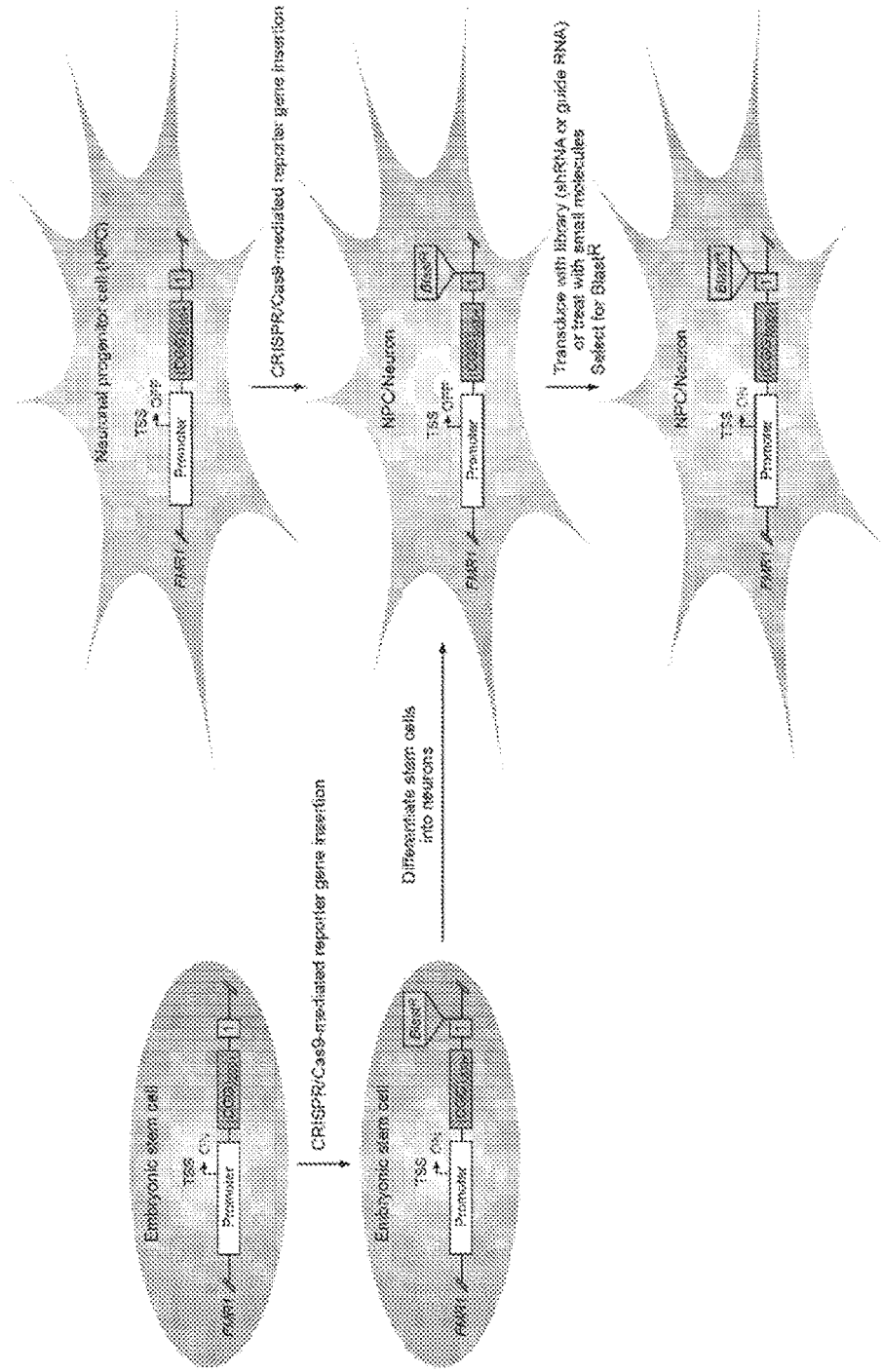
FIG. 5 shows a schematic of an unbiased, large-scale screen for factors that mediate epigenetic silencing of FMR1 gene.

A large-scale RNAi screen, using genome-wide libraries and/or kinase or transcription factor sub-libraries, is performed to identify new factors that mediate epigenetic silencing of FMR1 (FIG. 5). For this screen, a reporter cell line is derived, containing a blasticidine reporter gene (Blast®) positioned downstream of an inactivated FMR1 gene. Reactivation of the FMR1 gene by an epigenetic modulator of FMR1 induces expression of the Blast® gene and enables the isolation of positive candidates by drug selection. As shown in FIG. 5, the Blast® gene can be inserted into the FMR1 gene using a CRISPR/Cas9 system.

Example 3. A Candidate-Based Screen Identifies Epigenetic Regulators that Mediate Silencing of FMR1 in Patient-Derived Induced Pluripotent Stem Cells (iPSCs)

To identify epigenetic regulators that mediate silencing of FMR1, a small-scale short hairpin RNA (shRNA) library comprising 162 shRNAs directed against 33 well-characterized epigenetic regulators that mediate transcriptional repression was assembled. Each shRNA was packaged into lentivirus and transduced into an undifferentiated FXS iPSC line (FXS 848-iPS3 cells). Twenty days post-transfection, mRNA was prepared and FMR1 expression analyzed by quantitative RT-PCR (qRT-PCR). Positive results were considered to be statistically significant increases in FMR1 expression with at least two unrelated shRNAs directed against the same target compared to that obtained with a control non-silencing (NS) shRNA. The results of FIG. 4A identified nine epigenetic regulators of the silenced FMR1 gene: DNMT1, EZH2, RNF2 (also called RING1B), SUV39H1, KDM5C, KDM5D, HDAC5, HDAC10 and SIRT5, whose functions are briefly described in Table 4. For convenience, below factors that promote FMR1 silencing are referred to as FMR1 Silencing Factors (FMR1-SFs).

TABLE 4

List of nine epigenetic regulators of the silenced FMR1 gene and their function

| Protein | Function |
| --- | --- |
| DNMT1 | DNA methyltransferase |
| EZH2 | Subunit of polycomb repressive complex 2 (PRC2), catalyzes H3K27 trimethylation |

TABLE 4-continued

List of nine epigenetic regulators of the silenced FMR1 gene and their function

| Protein | Function |
| --- | --- |
| RING1B/RNF2 | Polycomb group (PcG) protein, mediates monoubiquitination of histone H2A |
| SUV39H1 | Histone H3K9 methyltransferase |
| KDM5C | Histone H3K4 demethylase (di- and tri-demethylase) |
| KDM5D | Histone H3K4 demethylase (di- and tri-demethylase) |
| HDAC5 | Histone deacetylase |
| HDAC10 | Histone deacetylase |
| SIRT5 | Sirtuin family member, closely related to histone deacetylases |

Figure 6B:
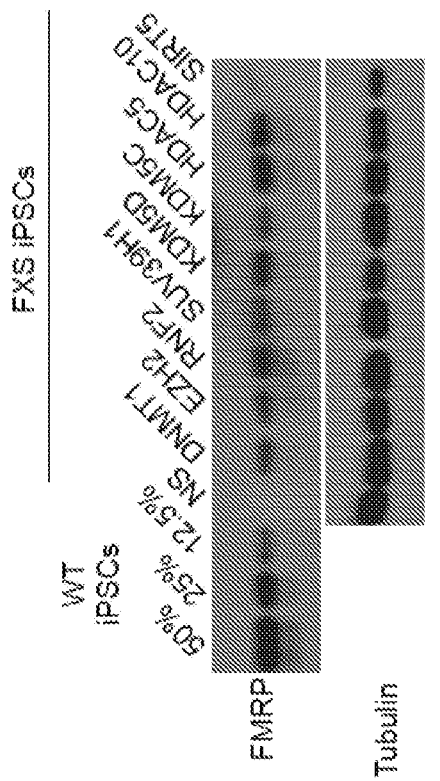
FIGS. 6A-6E shows a small-scale candidate-based screen identifies epigenetic regulators that mediate silencing of FMR1 in patient-derived iPSCs.
Figure 6A:
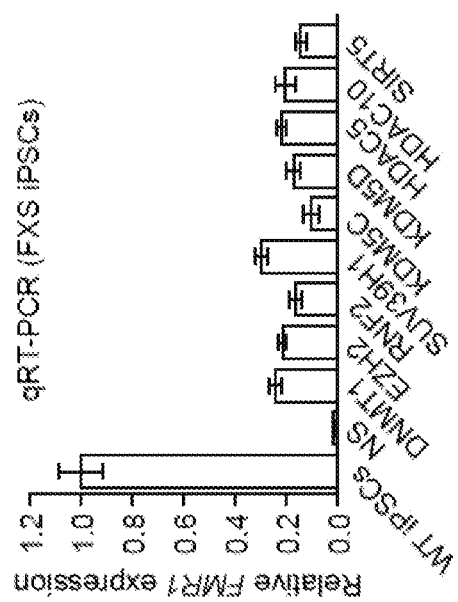
Figure 6C:
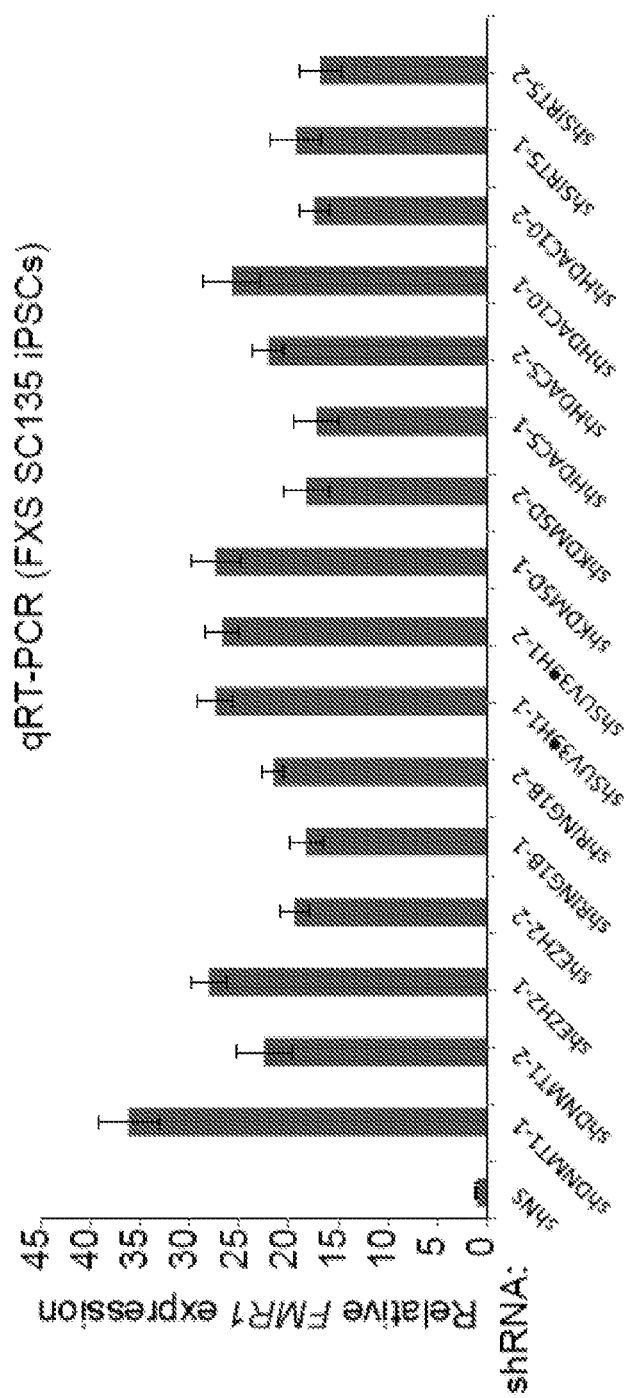
Figure 6D:
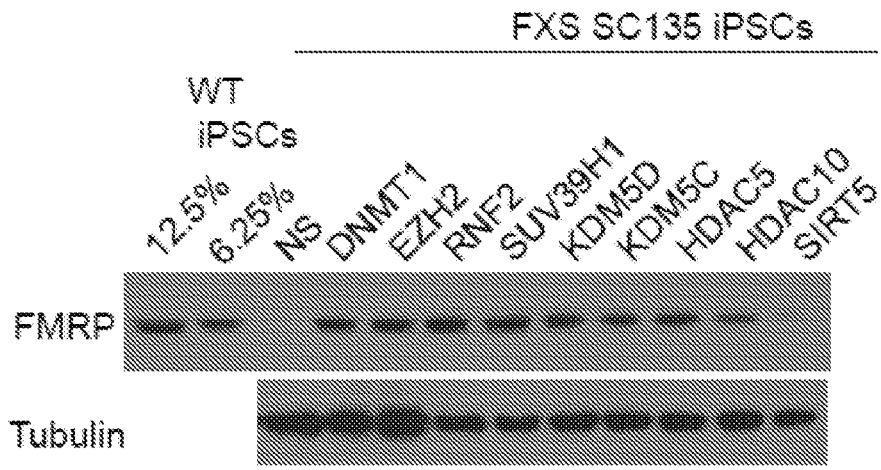

To determine the level of FMR1 reactivation obtained following shRNA-mediated knockdown of an FMR1-SF, an iPSC line derived from a normal individual (BJ1-iPS4) was analyzed in parallel. The qRT-PCR results of FIG. 6A show that shRNA-mediated knockdown of an FMR1-SF reactivated the epigenetically silenced FMR1 gene to ~20% of normal levels, which is within the range predicted to have clinical benefit. The immunoblot results of FIG. 6B show that knockdown of an FMR1-SF in FXS 848-iPS3 cells also restored FMRP protein to 15-20% of normal levels. Reactivation of epigenetically silenced FMR1 following knockdown of the nine FMR1-SFs was confirmed by qRT-PCR and immunoblotting in a second, unrelated FXS iPSC cell line, SC135 cells (FIGS. 6C-6D).

Figure 6E:
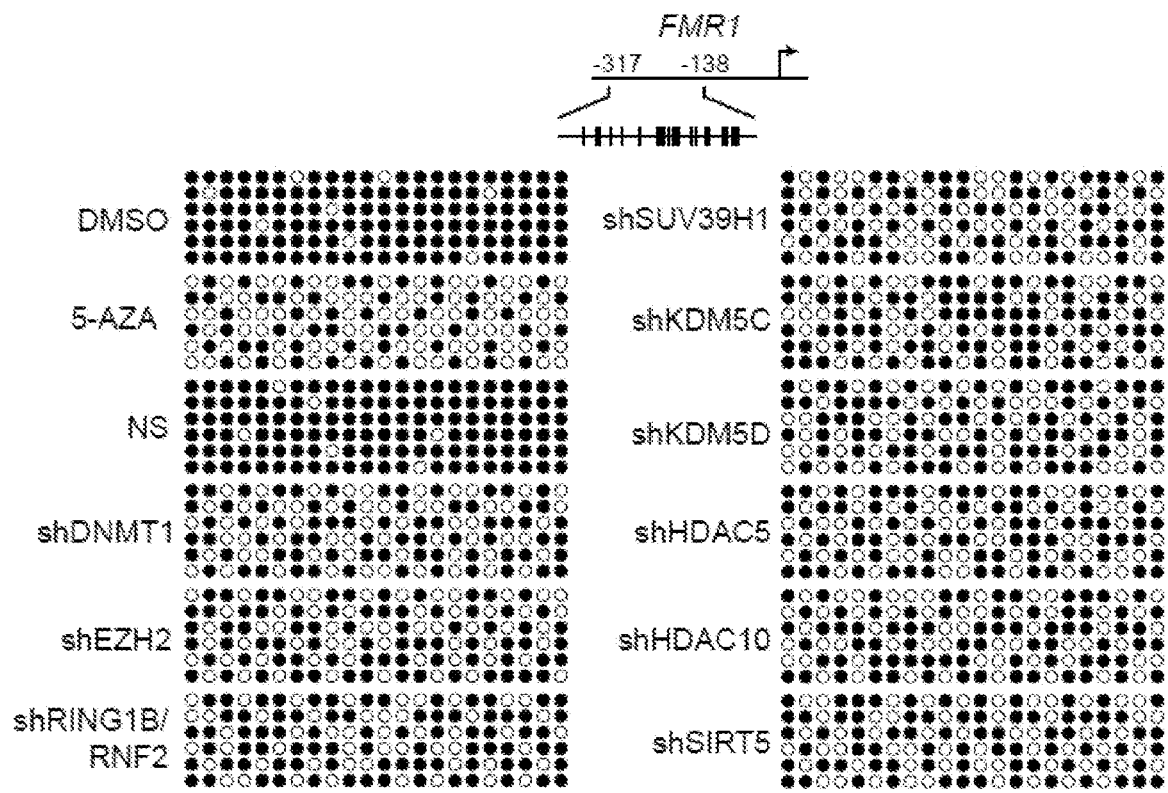

As described above, a characteristic feature of epigenetically silenced FMR1 is the presence of DNA hypermethylation. The bisulfite sequencing experiment of FIG. 6E confirms the DNA hypermethylation of the FMR1 promoter in the FXS iPSC cell line, FXS 848-iPS3. Consistent with previous studies, treatment of FXS 848-iPS3 cells with the DNA methyltransferase inhibitor 5-azacytidine led to a substantial decrease in DNA hypermethylation. Notably, there was a similar decrease in DNA hypermethylation following knockdown of one of the nine FMR1-SFs.

Figure 7A:
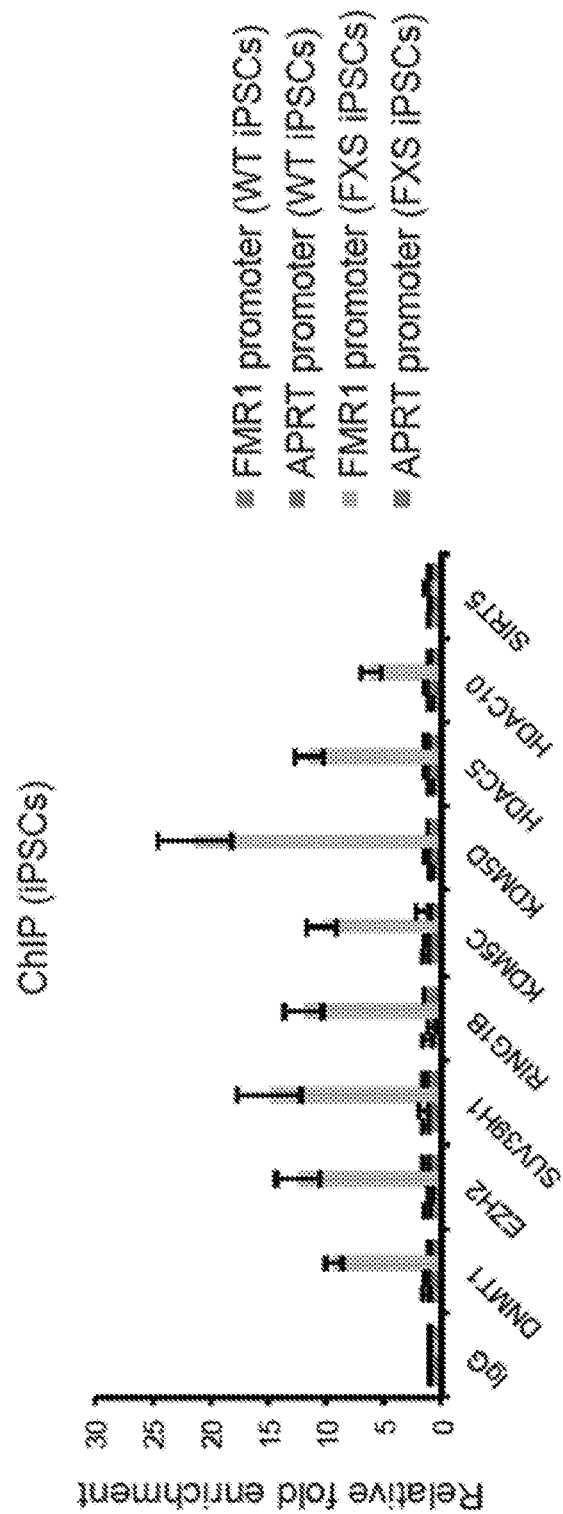

Example 4. The FMR1-SFs Stably Associate with Epigenetically Silenced FMR1 Through an Ordered Pathway Epigenetic regulators are typically stably associated with the promoters and/or genes upon which they act. To determine whether the nine FMR1-SFs are stably associated with the epigenetically silenced FMR1 promoter, a series of chromatin immunoprecipitation (ChIP) experiments were performed. The ChIP experiment of FIG. 7A shows that eight of the nine FMR1-SFs are bound to the epigenetically silenced FMR1 promoter in FXS iPSCs but not normal iPSCs. The FMR1-SFs were not bound to a negative control promoter of a constitutively active gene, APRT. The single FMR1-SF that is not associated with the epigenetically silenced FMR1 promoter is SIRT5, which is known to localized to the mitochondria. Thus, although SIRT5 promotes FMR1 silencing unlike the other FMR1-SFs it functions indirectly.

Figure 7B:
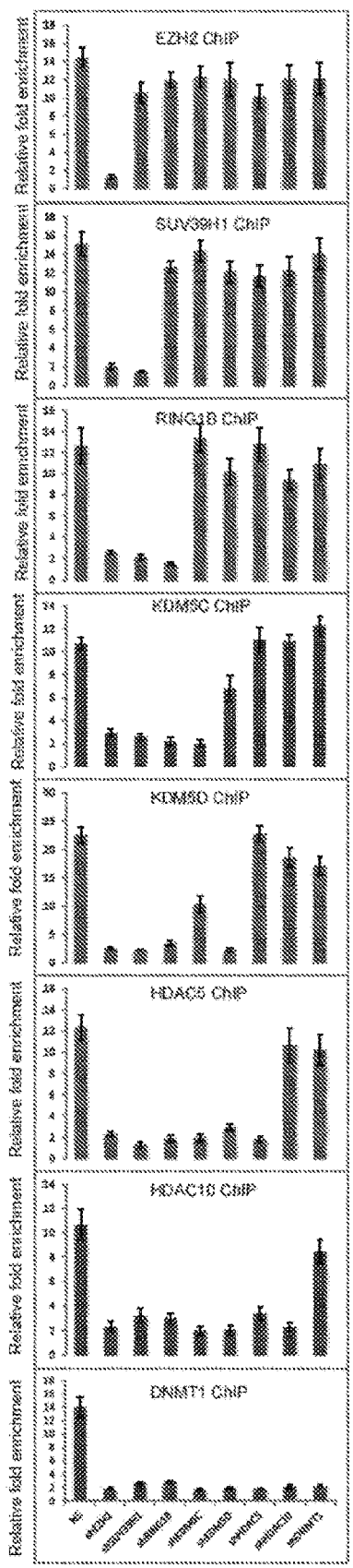
Figure 7C:
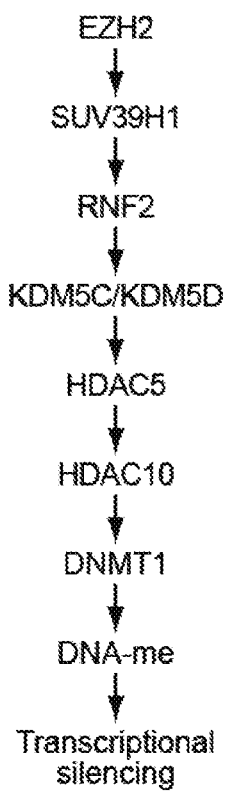

It has been previously shown that that repressive epigenetic regulators are recruited to promoters in an ordered pathway. To determine whether the FMR1-SFs are recruited to FMR1 in a pathway, single FMR1-SFs were knocked down and then the binding of all FMR1-SFs (except SIRT5) was analyzed in a ChIP assay. These results, which are presented in FIG. 7B, show that the FMR1-SFs are sequentially recruited to the FMR1 promoter in a pathway that is summarized in FIG. 7C. For example, knockdown of EZH2, the first FMR1-SF to associate with FMR1, results in the loss of recruitment of all other FMR1-SFs. By contrast, knockdown of DNMT1, the last FMR1-SF to associate with FMR1, does not affect recruitment of the other FMR1-SFs. Notably, in all of the previous studies on other epigenetically silenced genes it has been found that the DNMT is the last repressive epigenetic regulator to be recruited.

Figure 7D:
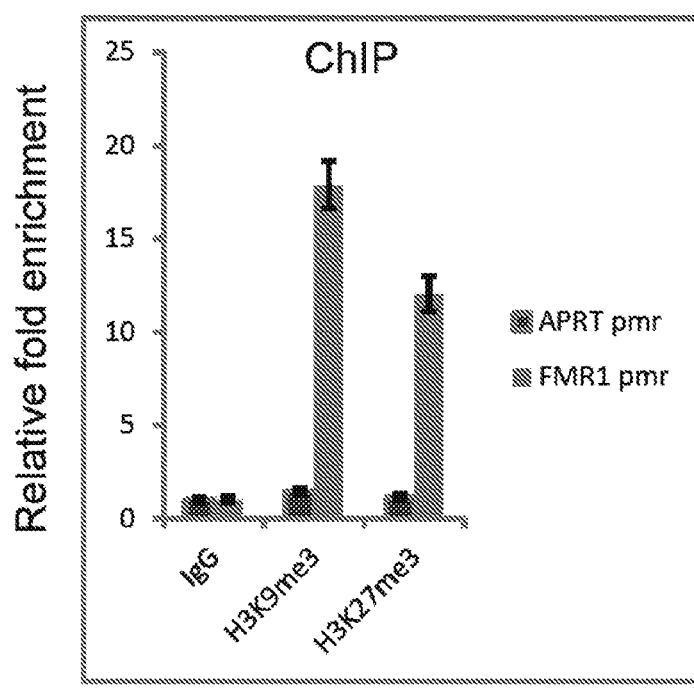
Figure 7E:
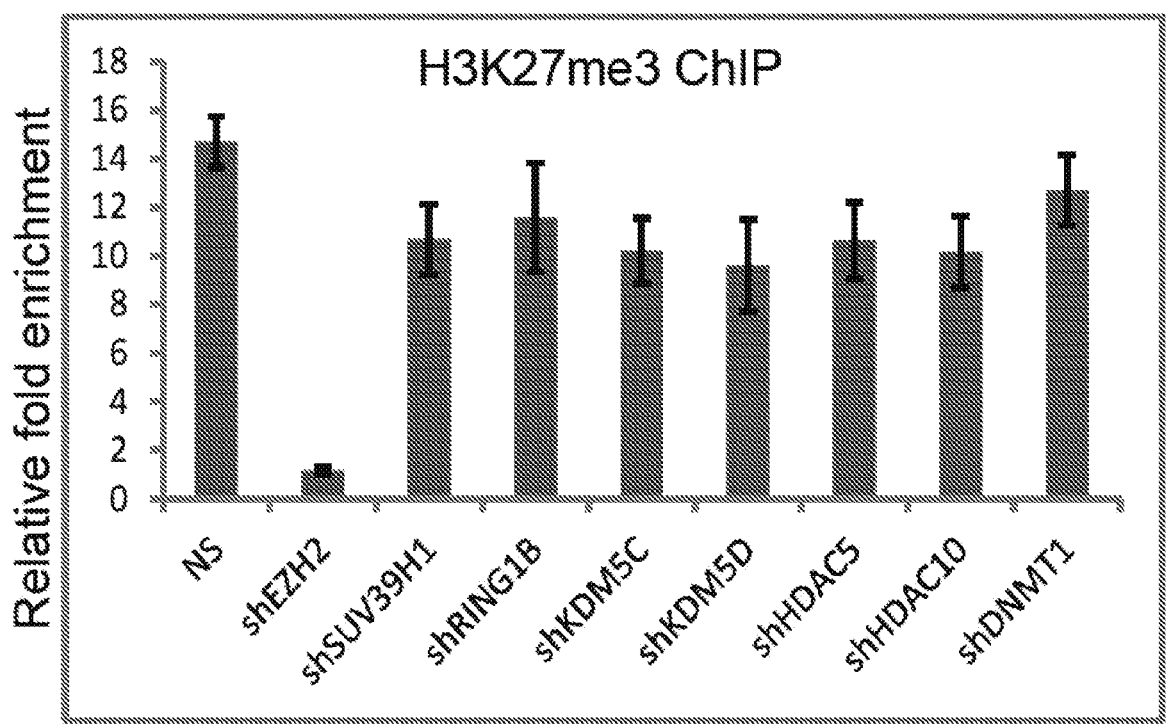
Figure 7F:
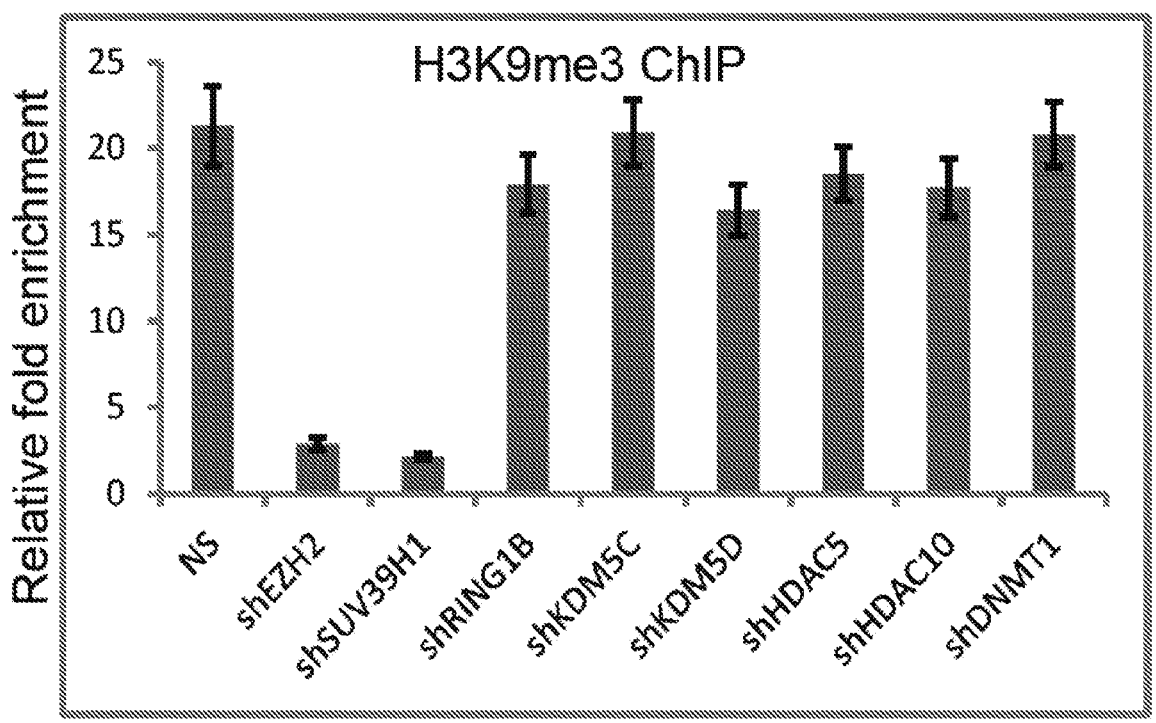

It has been previously shown that FMR1 silencing is accompanied with deposition of histone H3 lysine 9 trimethylation (H3K9me3) and histone H3 lysine 27 trimethylation (H3K27me3) on the FMR1 promoter. FIG. 7D shows that in FXS iPSCs detect H3K9me3 and H3K27me3 could be detected on the FMR1 promoter, but not a control promoter (APRT). FIG. 7E shows, as expected, that knockdown of EZH2, which catalyzes H3K27me3, resulted in decreased levels of H3K27me3 at the FMR1 promoter. By contrast, knockdown of any one of the other FMR1-SFs did not affect H3K27me3. FIG. 7F shows, as expected, that knockdown of SUV39H1, an H3K9 methyltransferase, resulted in decreased levels of H3K9me3 at the FMR1 promoter. In addition, knockdown of EZH2 also resulted in reduced H3K9me3 levels, consistent with the finding that EZH2 recruitment is required for SUV39H1 binding (see FIG. 7C).

Figure 8A:
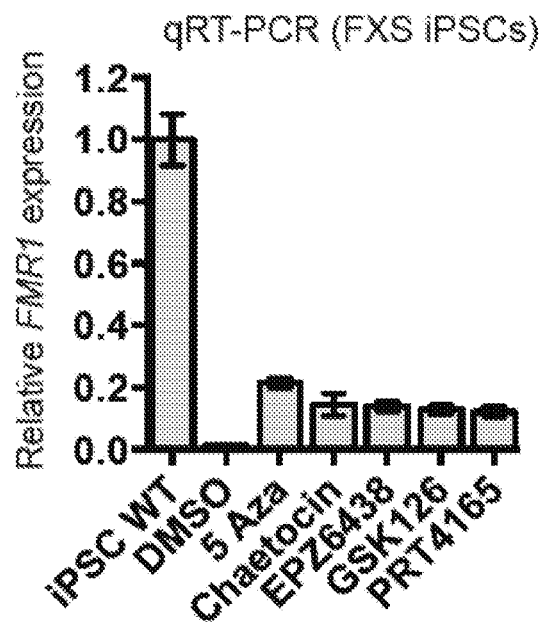
FIGS. 8A-8F show the reactivation of epigenetically silenced FMR1 by small molecule inhibitors of FMR1-SFs.
Figure 8B:
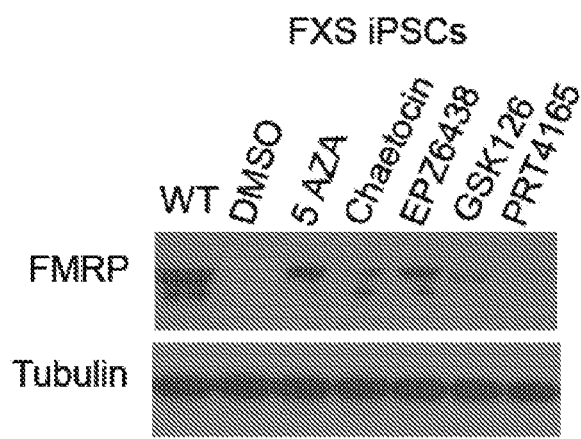
Figure 8C:
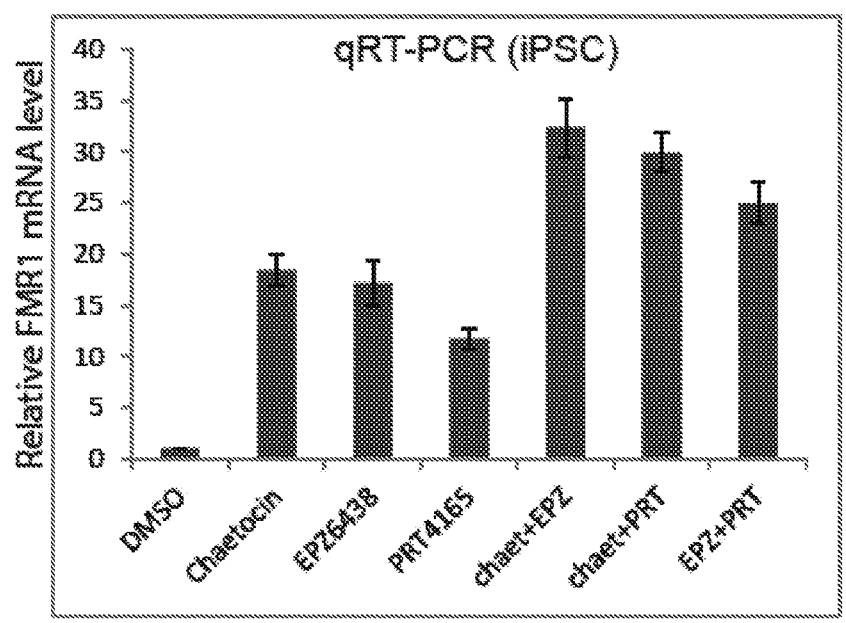

Example 5. Reactivation of Epigenetically Silenced FMR1 by Small Molecule Inhibitors of FMR1-SFs For several of the FMR1-SFs, there are well described small molecule inhibitors. FIG. 8A shows that epigenetically silenced FMR1 could be reactivated in FXS 848-iPS3 cells by treatment with the DNA methyltransferase inhibitor 5-azacytidine, consistent with the results of several previous studies. Notably, epigenetically silenced FMR1 was also reactivated following treatment with small molecule inhibitors of EZH2 (EPZ6438, GSK126), SUV39H1 (chaeotocin) and RNF2 (PRT4165). Reactivation was observed by analysis of both FMR1 mRNA (FIG. 8A) and protein (FIG. 8B) level and was again ~15-20% of wild-type levels. Interestingly, it was found that co-treatment with two inhibitors—such as chaeotocin and EPZ6438, chaeotocin and PRT4165, or EPZ6438 and PRT4165—resulted in enhanced reactivation of FMR1 compared to treatment with a single inhibitor alone (FIG. 8C).

Figure 8D:
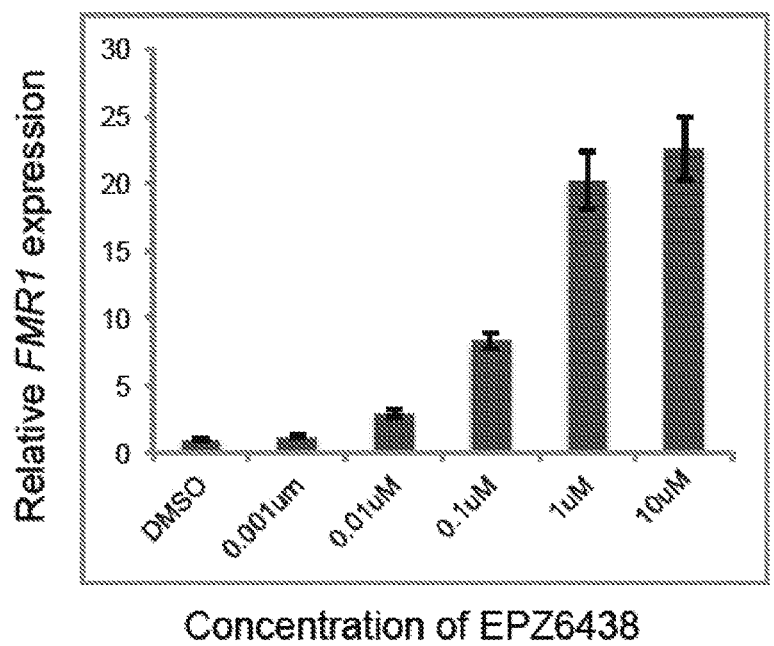
Figure 8E:
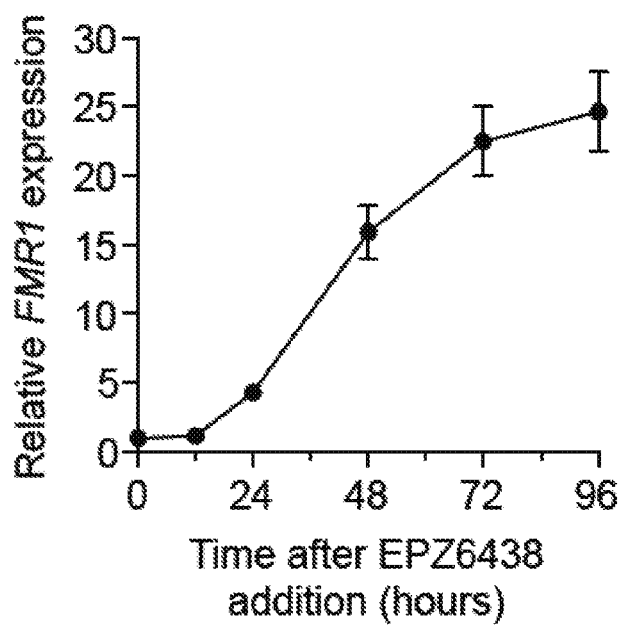
Figure 8E:
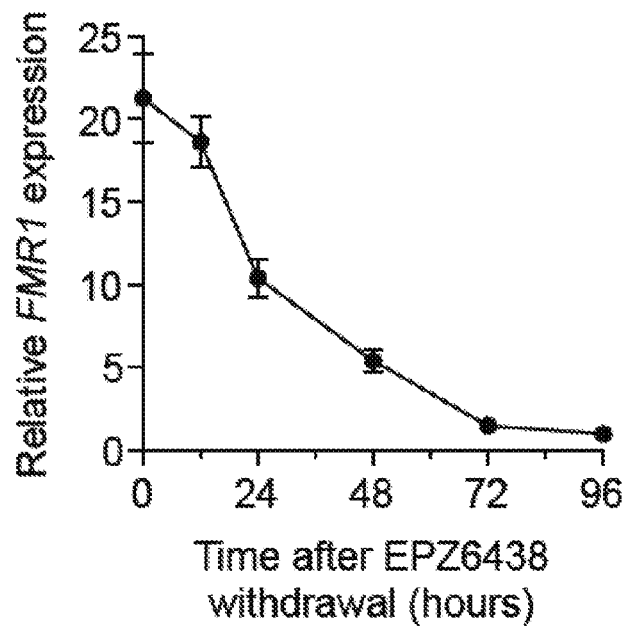
Figure 8F:
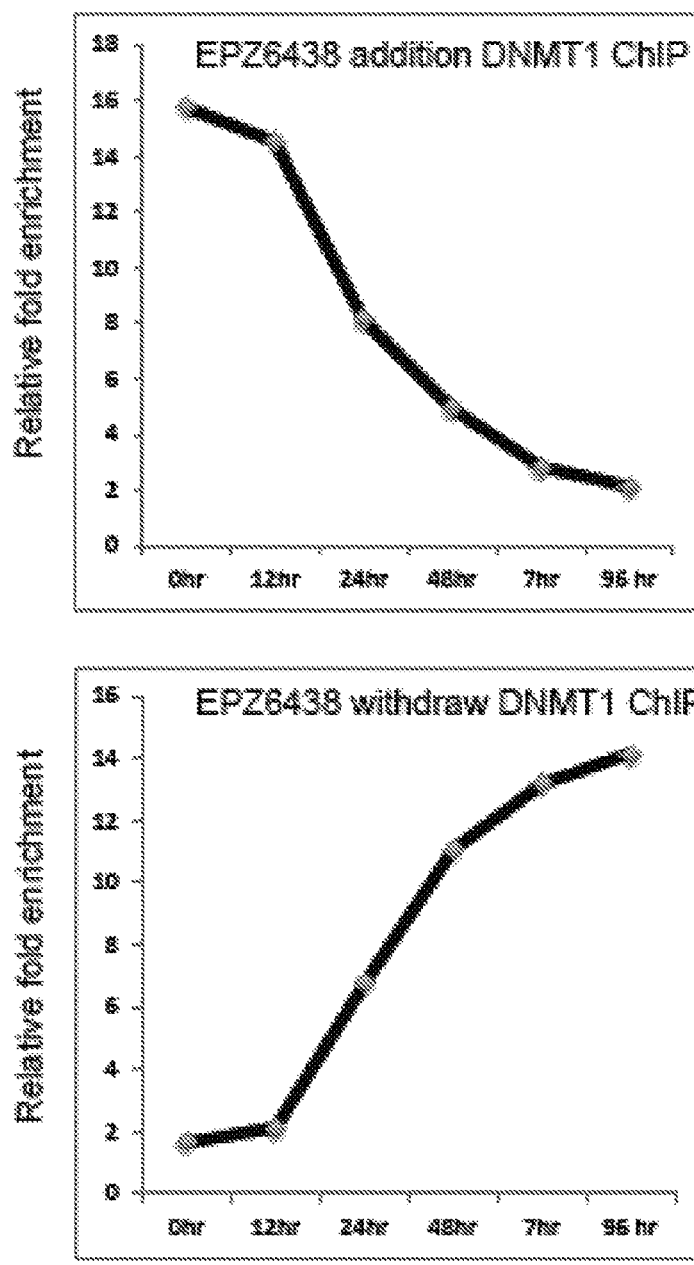

Several additional experiments with the EZH2 inhibitor EPZ6483, which is currently in several clinical trials. The EPZ6483 titration experiment of FIG. 8D shows that there is a very good correlation between the loss of EZH2 enzymatic activity and FMR1 reactivation. The time course experiment of FIG. 8E shows that following addition of EPZ6483, FMR1 reactivation increased over 96 hours at which point it began to plateau. Withdrawal of EPZ6483 resulted in re-silencing of FMR1, which again occurred over a time course of ~96 hours. Collectively, these results indicate that both silencing and reactivation of FMR1 are reversible processes. Finally, the CUP experiment of FIG. 8F shows that the association of DNMT1 with the FMR1 promoter is well correlated with the kinetics of FMR1 silencing following EPZ6483 addition and FMR1 reactivation following EPZ6483 withdrawal.

Figure 9A:
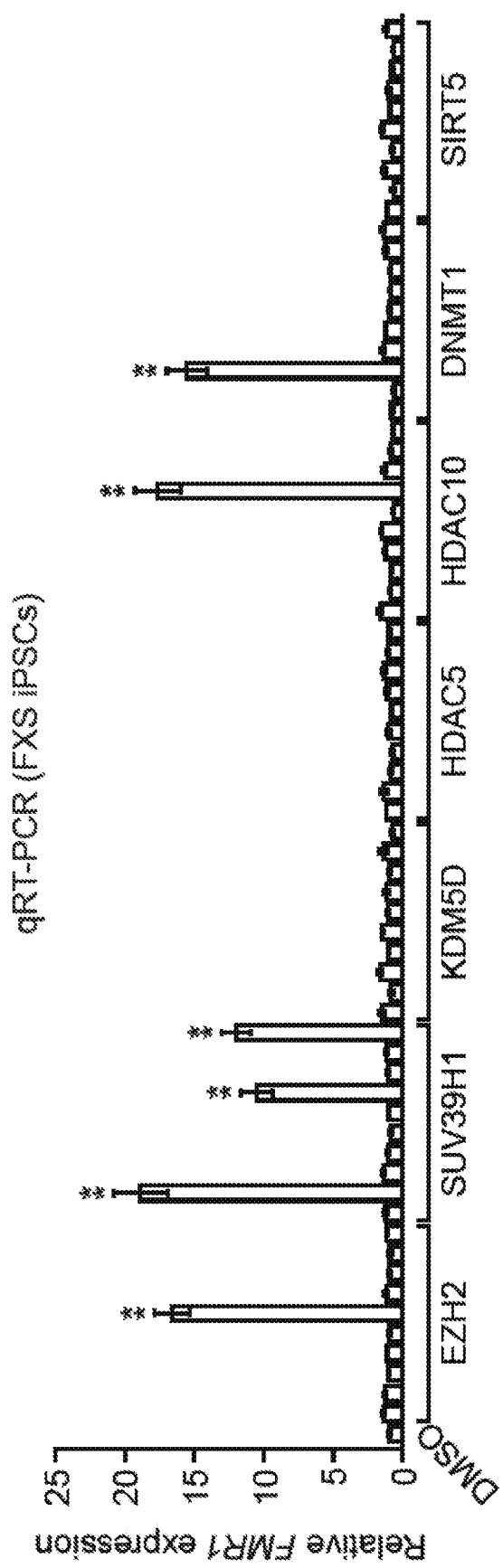
FIGS. 9A-9D show the identification of additional small molecule inhibitors from the epigenetics targeted library (Life Chemicals) that reactivate FMR1.
Figure 9B:
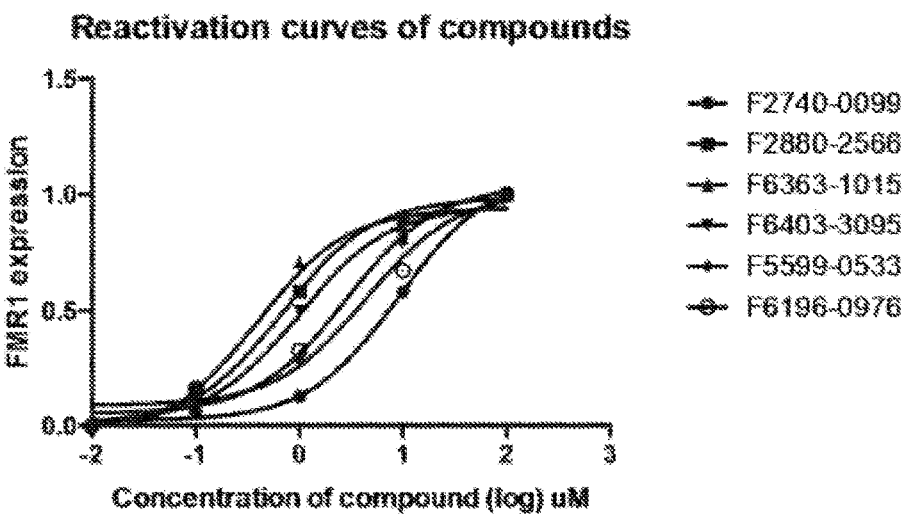
Figure 9C:
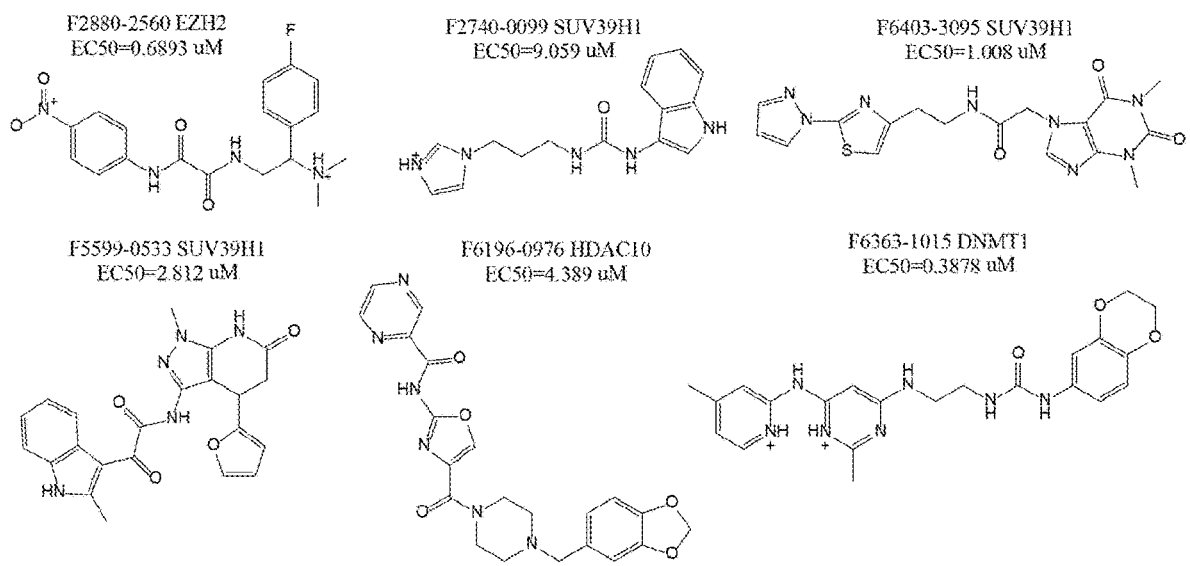
Figure 9D:
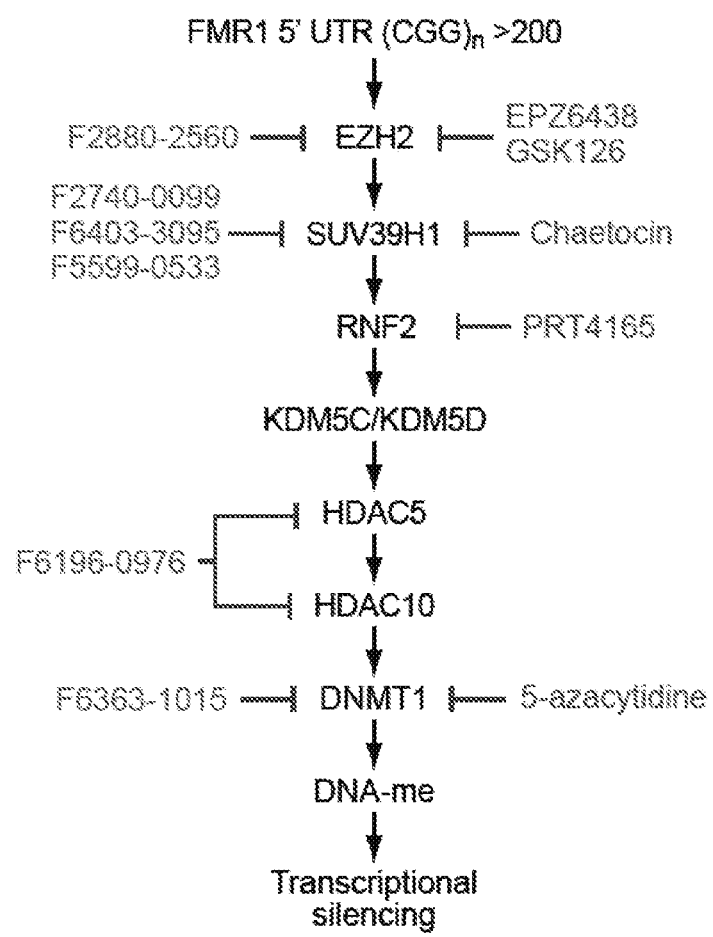

To identify additional small molecule inhibitors that reactivate FMR1, a panel of compounds from the Epigenetics Targeted Library (Life Chemicals) that were chosen based on virtual docking and similarity search were screened. FIG. 9A shows that a total of six compounds targeting EZH2 (F2880-2560), SUV39H1 (F2740-0099, F6403-3095, F5599-0533), HDAC10 (F6196-0976) and DNMT1 (F6363-1015) reactivated the epigenetically silenced FMR1 gene. The titration assay of FIG. 9B shows the reactivation of FMR1 is dose-dependent. The structures of identified compounds are not close to each other (FIG. 9C). Examples of the small molecules that can reactivate silenced FMR1 is shown in FIG. 9D.

Figure 10A:
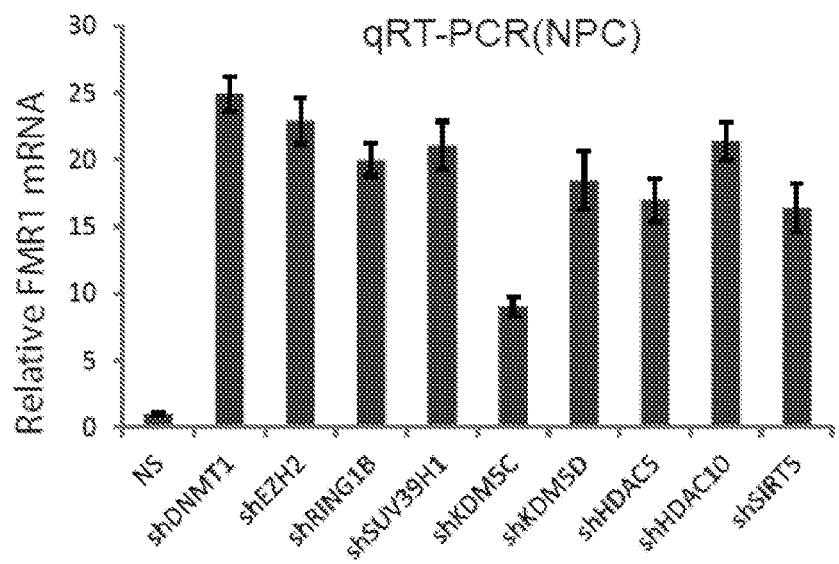
FIGS. 10A-10D show the FMR1-SFs also mediate epigenetic silencing of FMR1 in FXS neural progenitor cells (NPCs).
Figure 10B:
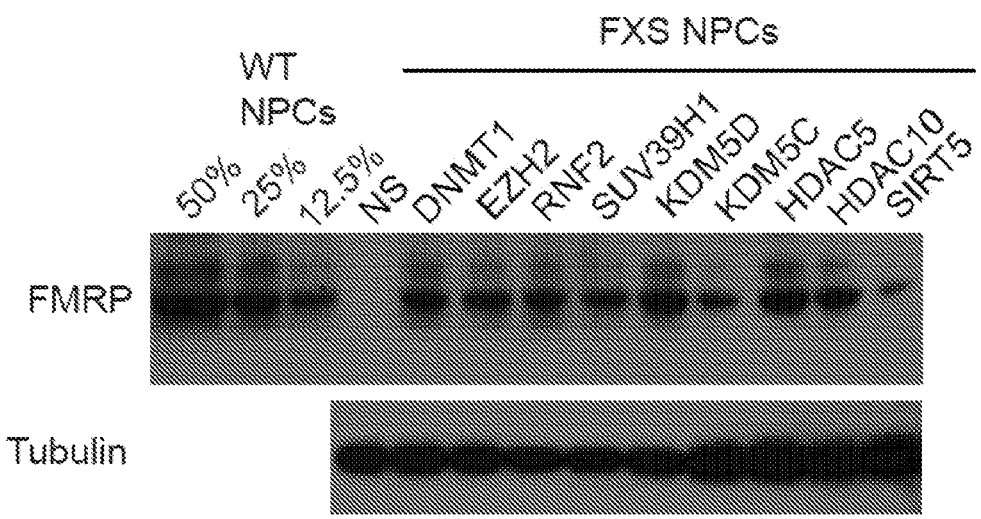
Figure 10C:
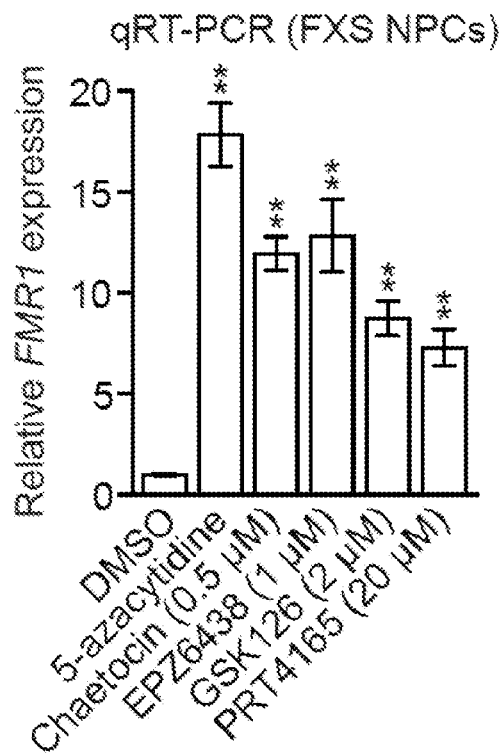
Figure 10D:
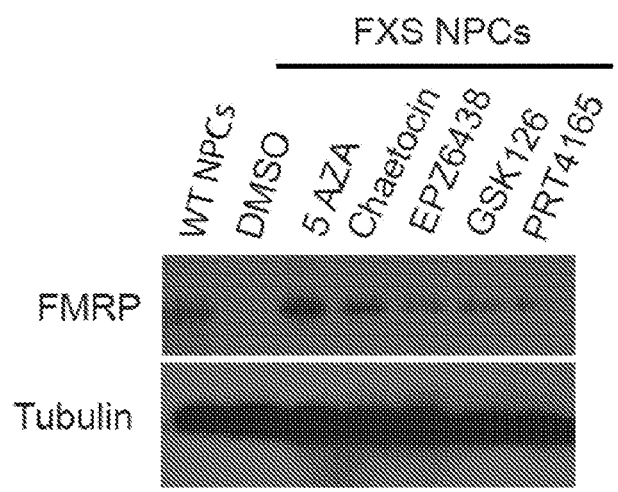

Example 6. The FMR1-SFs Also Mediate Epigenetic Silencing of FMR1 in FXS Neural Progenitor Cells (NPCs) and Post-Mitotic Neurons The experiments described above were performed in undifferentiated FXS iPSCs. Whether antagonism of the same set of FMR1-SFs would also reactivate epigenetically silenced FMR1 in FXS NPCs and post-mitotic neurons, the latter of which is a particularly relevant cell type for FXS, was next examined. For these experiments, an FXS NPC cell line that was derived from the FXS 848-iPS3 cells described above was used. Knockdown of any one of the nine FMR1-SFs reactivated epigenetically silenced FMR1 in FXS 848-NPCs at both the mRNA (FIG. 10A) and protein (FIG. 10B) levels. Epigenetically silenced FMR1 was also reactivated at the mRNA and protein levels in FXS 848-NPCs by small molecule inhibitors of FMR1-SFs including 5-azacytidine, chaeotocin, EPZ6483, GSK126 and PRT4165 (FIGS. 10C-10D).

Figure 11A:
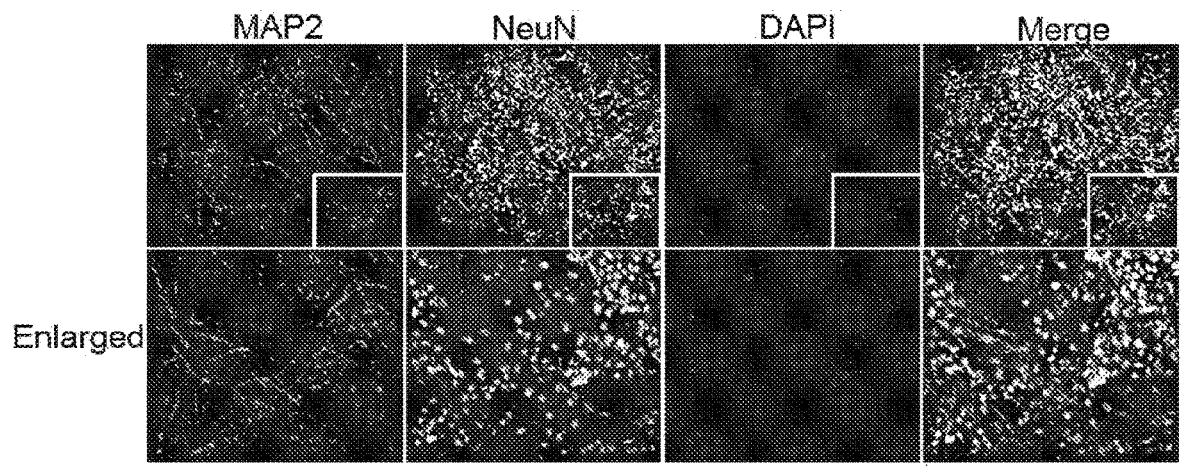
FIGS. 11A-11G shows that the FMR1-SFs also mediate epigenetic silencing of FMR1 in FXS post-mitotic neurons.
Figure 11B:
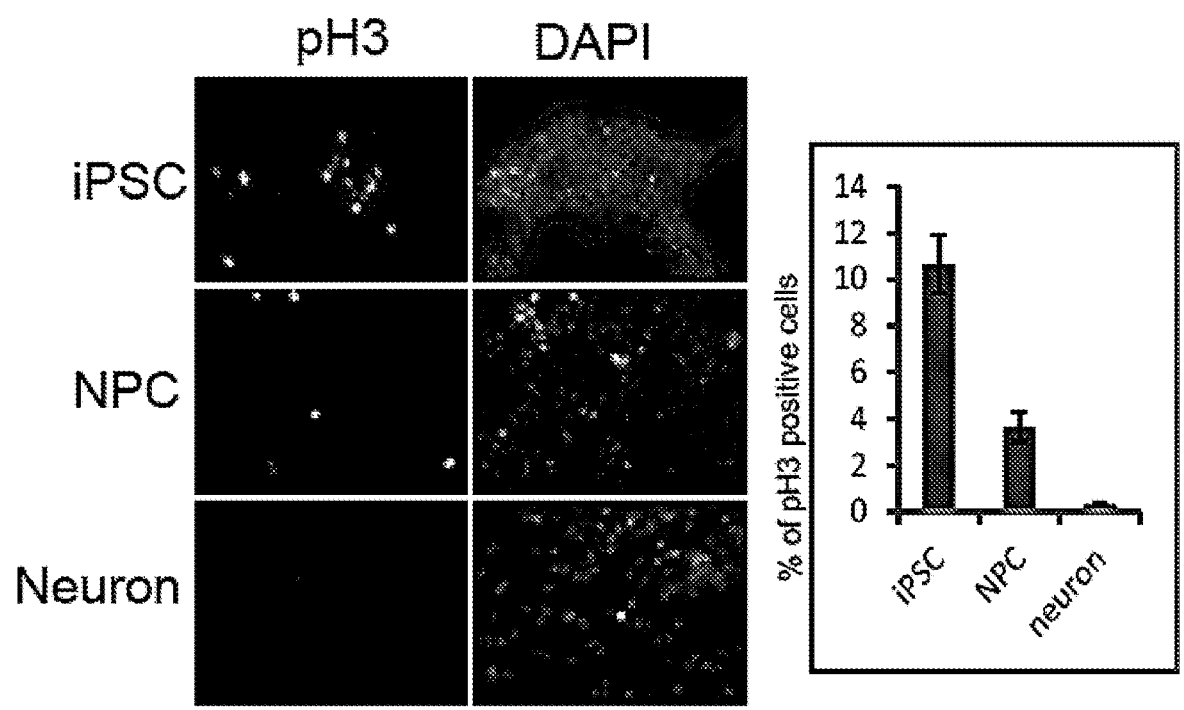
Figure 11C:
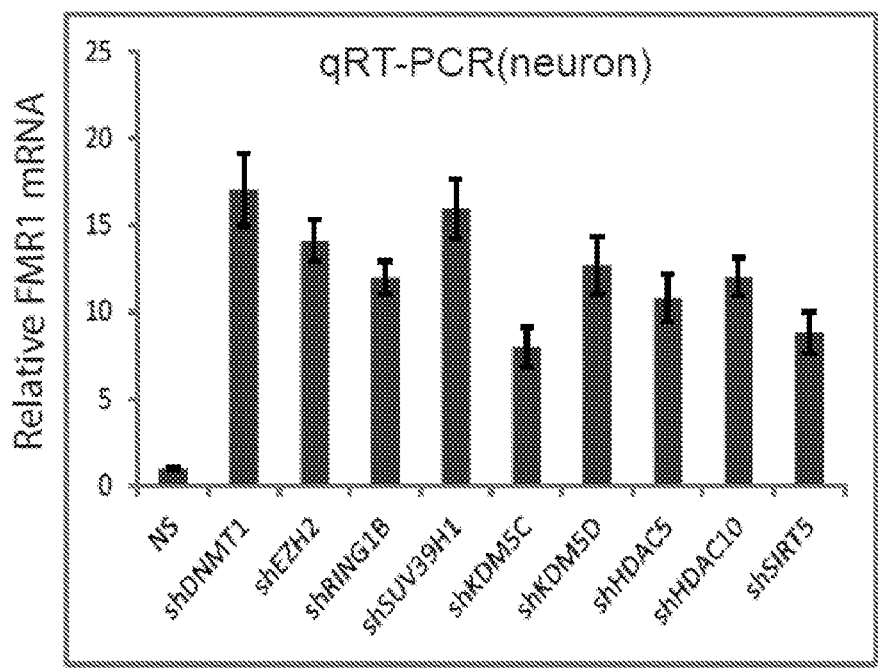
Figure 11D:
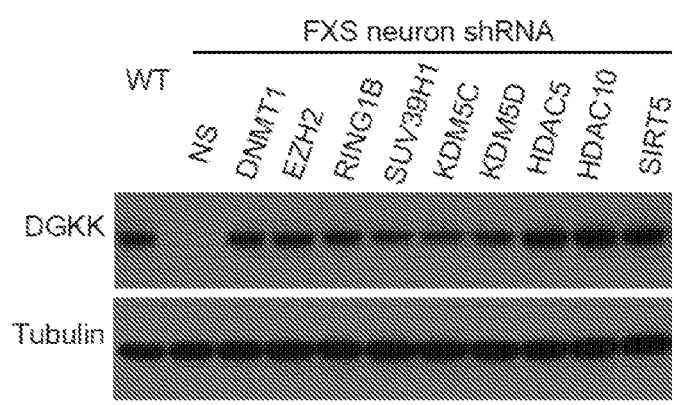
Figure 11E:
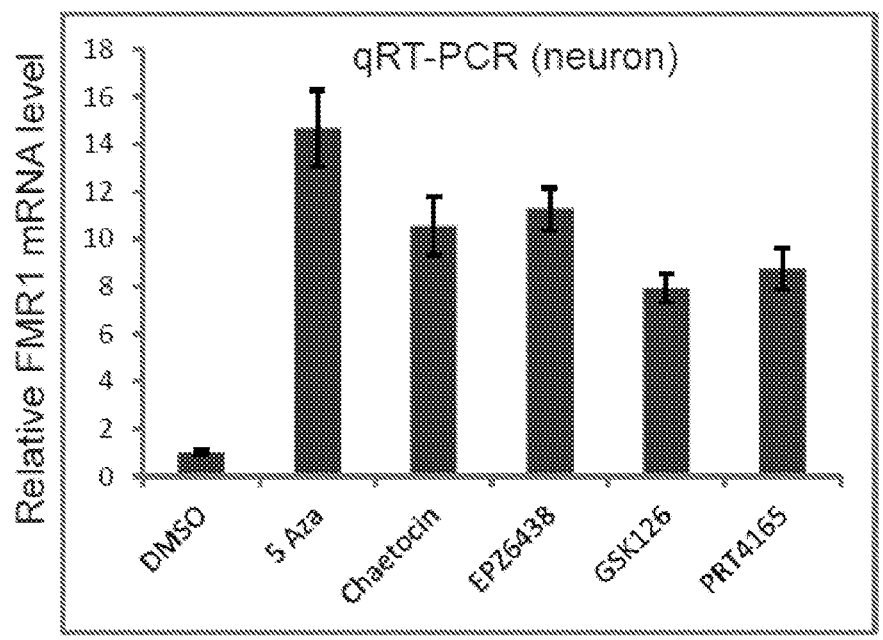
Figure 11F:
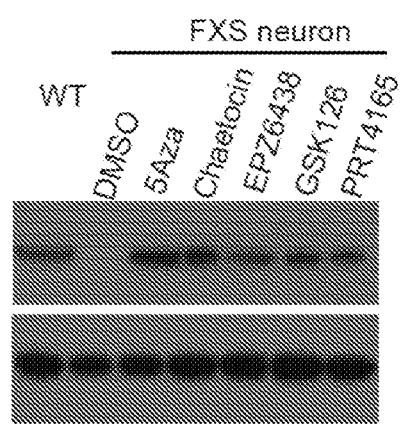
Figure 11G:
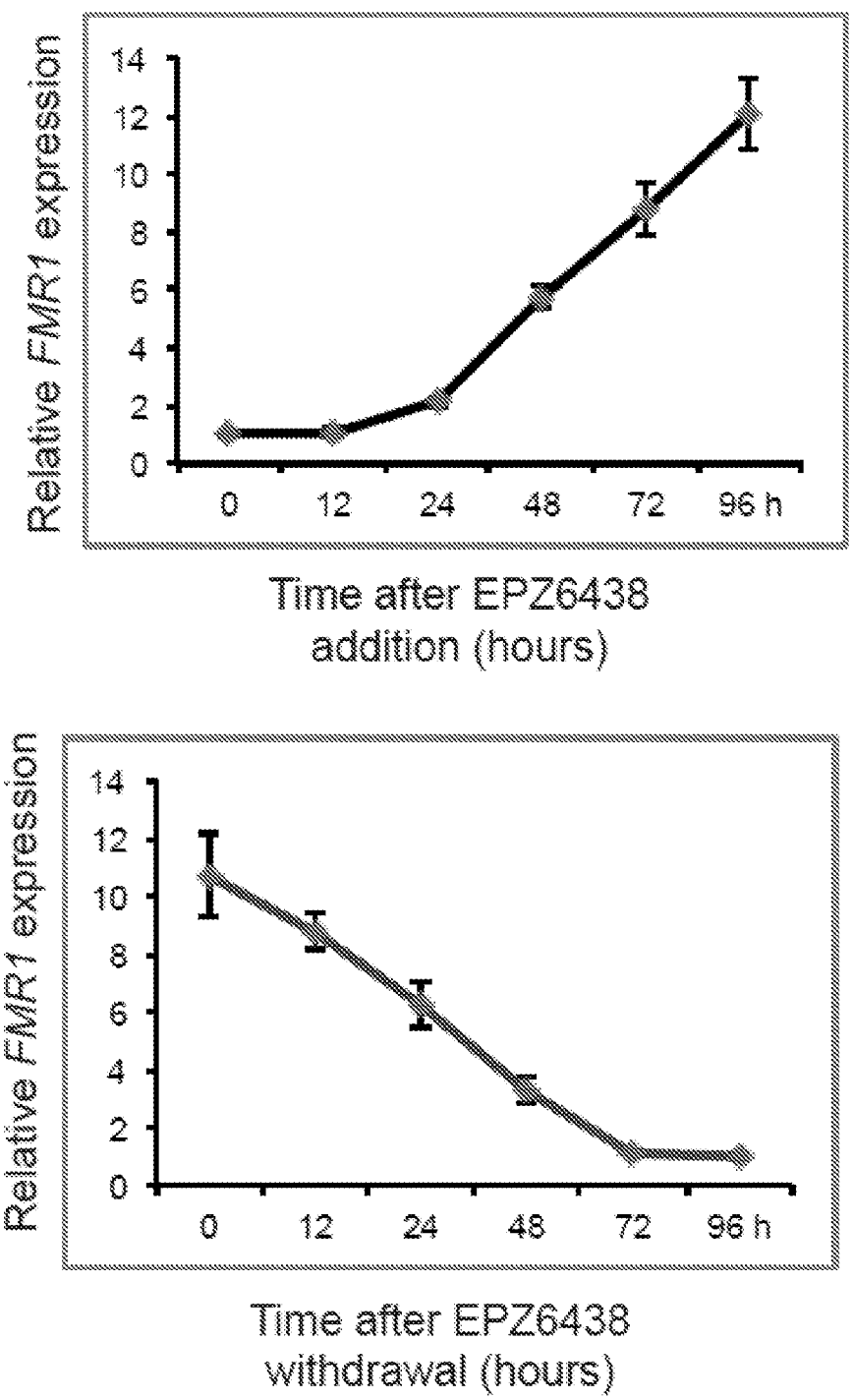

To derive FXS post-mitotic neurons, the FXS 848-NPCs were cultured in the absence of the mitogens EGF and bFGF. Neuronal differentiation was confirmed by staining with the neuronal markers MAP2 and NeuN (FIG. 11A). As expected, the FXS 848-NPC-derived neurons were post-mitotic as evidenced by the lack of staining with an antibody directed the mitotic marker phosphorylated H3 (FIG. 11B). Knockdown of the nine FMR1-SFs reactivated epigenetically silenced FMR1 in FXS 848-NPC-derived post-mitotic neurons at both the mRNA (FIG. 11C) and protein (FIG. 11D) levels. Epigenetically silenced FMR1 was also reactivated in FXS 848-NPC-derived post-mitotic neurons by small molecule inhibitors of FMR1-SFs including 5-azacytidine, chaeotocin, EPZ6483, GSK126 and PRT4165 at the mRNA (FIG. 11E) and protein (FIG. 11F) levels. Similar to what was found in FXS iPSCs, in FXS 848-NPC-derived post-mitotic neurons reactivation of epigenetically silenced FMR1 with the EZH2 inhibitor EPZ6483 occurred over a time course of ~96 hours and was reversible (FIG. 11G).

Example 7. FMR1 Reactivation can Normalize the Dysfunctional FXS Neuronal Phenotype Whether the partial reactivation of FMR1 by shRNAs or small molecule inhibitors is sufficient to "normalize" the dysfunctional FXS neuronal phenotype was next examined. The physiological relevance of the results were determined using several quantifiable measures of the FXS neuronal phenotype in FXS iPSC-derived neurons.

Figure 12A:
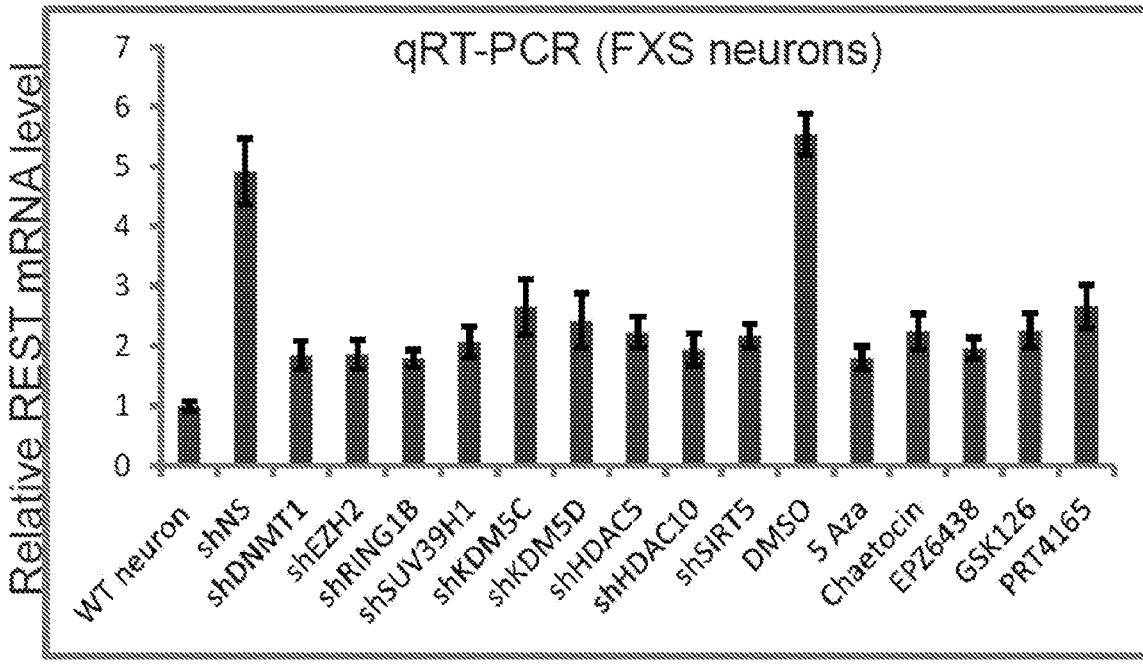
FIGS. 12A-12F shows that FMR1 reactivation can normalize the dysfunctional FXS neuronal phenotype.
Figure 12B:
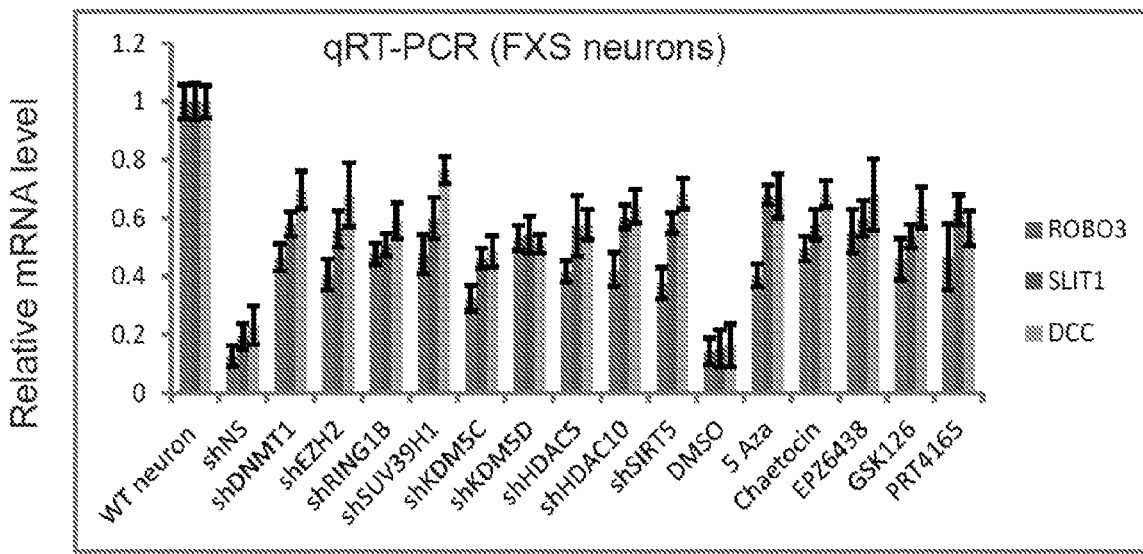

First, alterations in gene expression of the neural transcriptional repressor REST and its target axonal guidance genes were measured. REST is a master negative regulator of neurogenesis, regulating the pool size and timing of differentiation of different neural lineages. REST is expressed in embryonic stem cells (ESCs), NPCs, and non-neuronal cells, where it suppresses neuron-specific genes, in contrast to differentiated neurons where it is silenced. However, in FXS-derived neurons, REST levels are high, resulting in the suppression of axonal guidance genes as well as other genes important for proper axon development. In FXS iPSC-derived neurons, treatment with FMR1-SF shRNAs or inhibitors resulted in a decrease in REST expression relative to control treatments (FIG. 12A) and an increase in REST target axonal guidance genes ROBO3, SLIT1 and DCC (FIG. 12B).

Figure 12C:
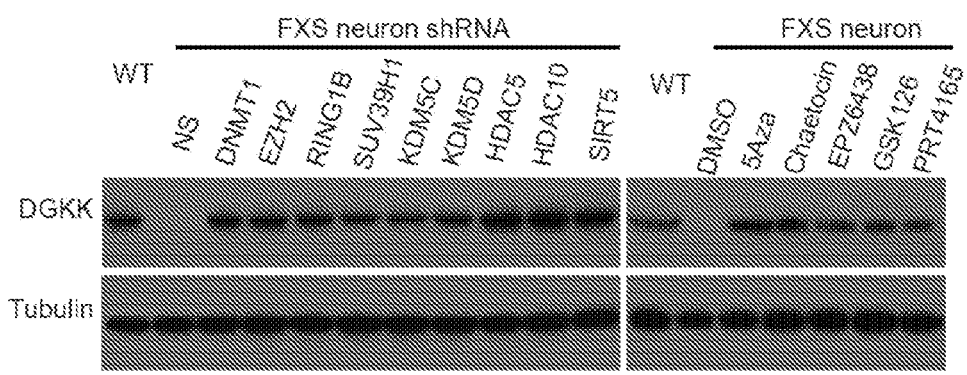

Second, protein levels of diacylglycerol kinase kappa (DGKκ), a master regulator that controls the switch between diacylglycerol and phosphatidic acid signaling pathways were measured. The absence of FMRP in FXS neurons results in decreased levels of DGKκ, which is sufficient to cause dendritic spine abnormalities, synaptic plasticity alterations, and behavior disorders similar to those observed in the FXS mouse model. Moreover, ectopic expression of DGKκ rescues the dendritic spine defects of FMR1 KO neurons. FIG. 12C shows that treatment of FXS iPSC-derived neurons with FMR1-SF shRNAs or inhibitors resulted in an increase in DGKκ to levels comparable to those found in wild-type neurons.

Figure 12D:
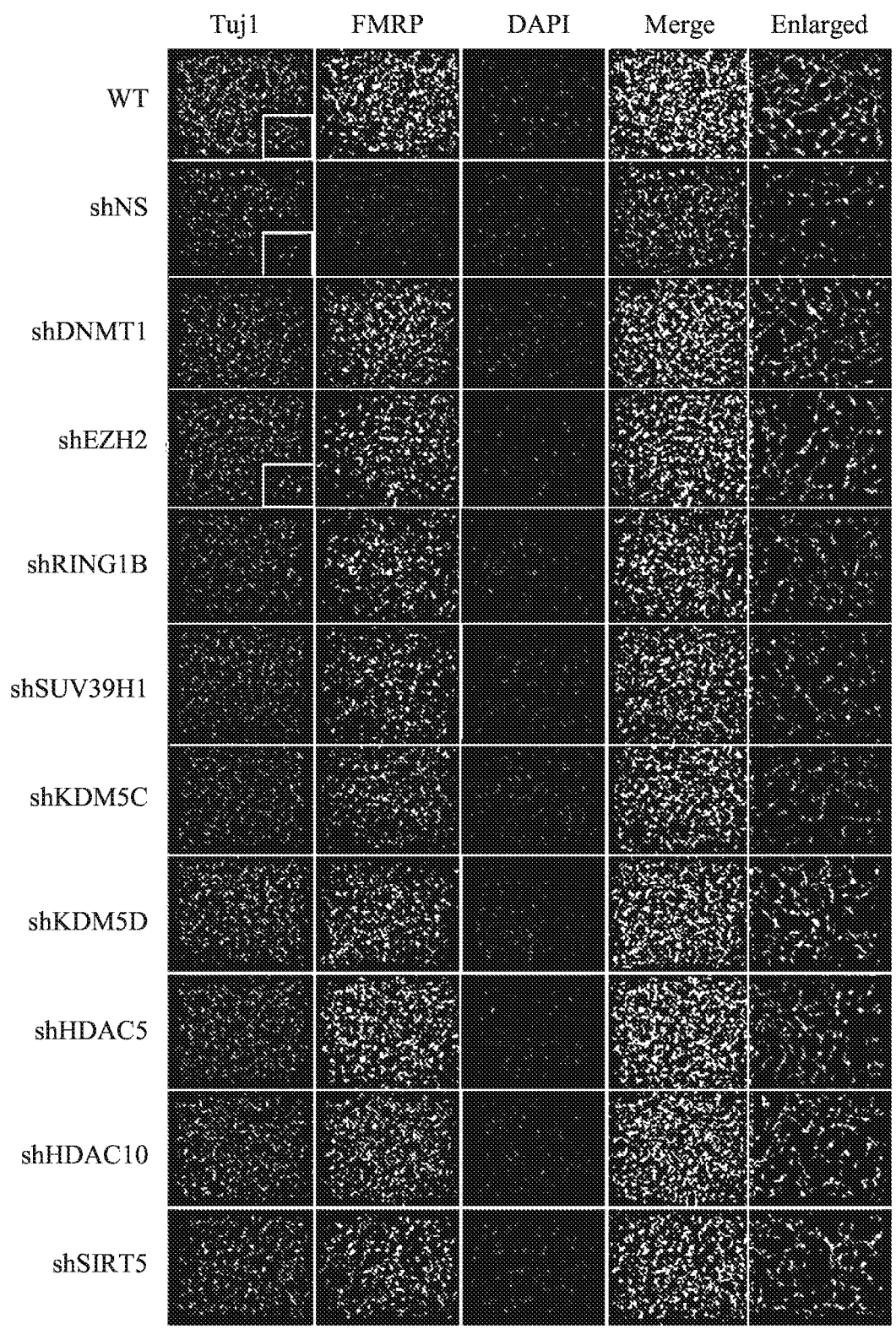
Figure 12E:
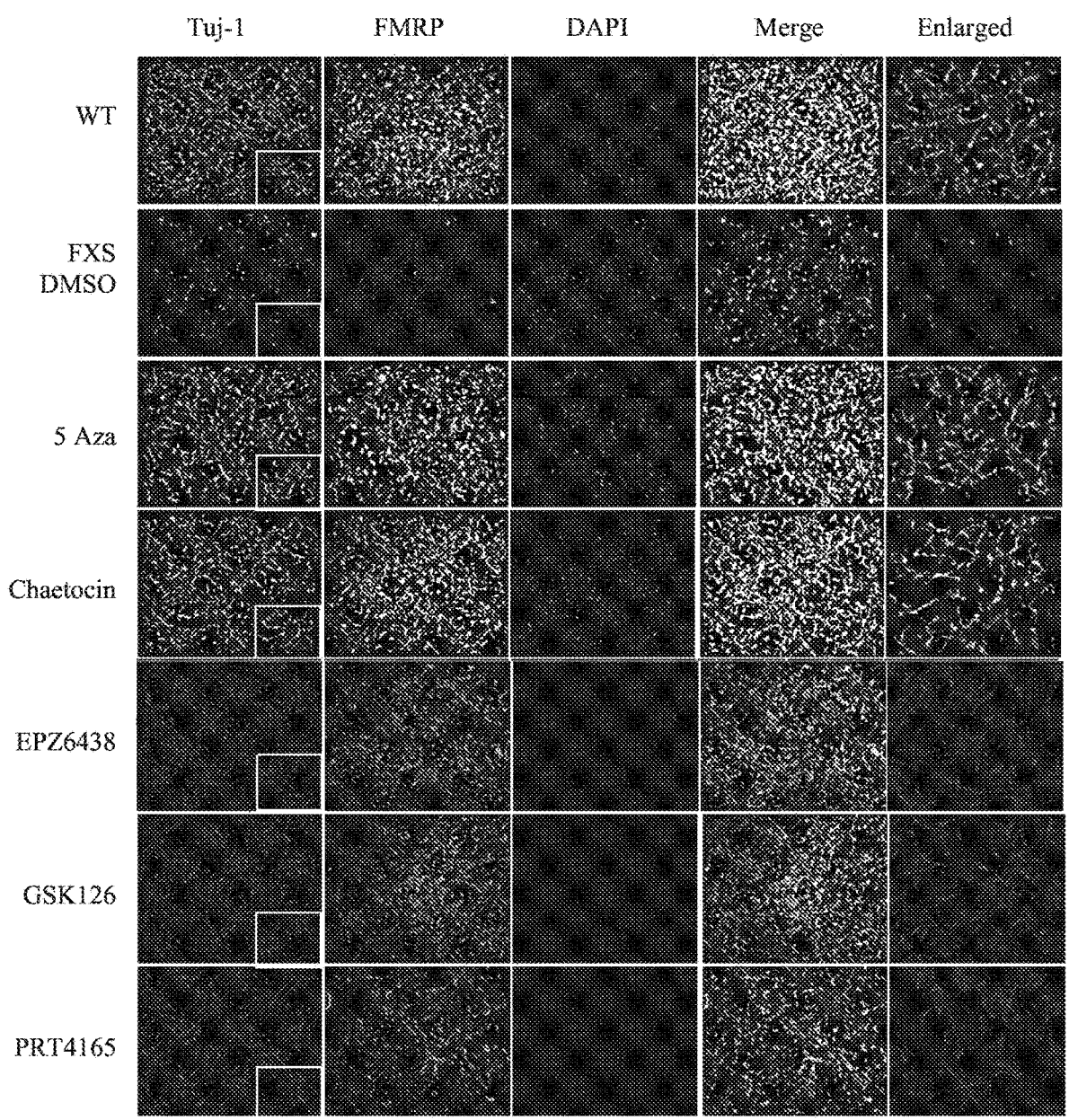
Figure 12F:
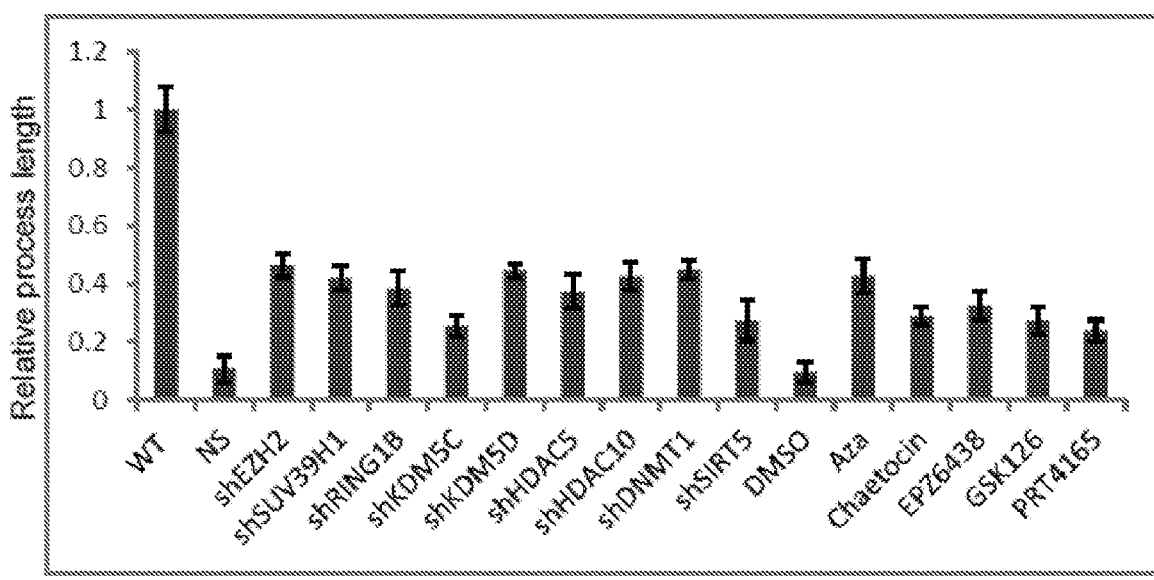

Finally, studies to determine whether FMR1-SF shRNAs and inhibitors could rescue aspects of neuronal morphology (soma area, soma perimeter, neurite process length, neurite branch points, secondary projections) that are abnormal in FXS neurons were performed. As a first step, cells were stained with the neuronal marker TUJ1, which allowed the measurement of neurite process length Immunofluorescence analysis shows that TUJ1 and FMRP staining was restored in FXS iPSC-derived neurons by knockdown of an FMR1-SF (FIG. 12D) or treatment with an FMR1-SF inhibitor (FIG. 12E). Furthermore, treatment with FMR1-SF shRNAs or inhibitors resulted in an increase in neurite process length to levels approximately 25-45% those of wild-type iPSC-derived neurons (FIG. 12F).

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method for treating a FMR1-inactivation-associated disorder in a subject in need thereof, the method comprising: administering to the subject a therapeutically effective amount of an epigenetic modulator of FMR1, wherein the epigenetic modulator reactivates a transcriptionally inactive FMR1 gene in the subject, wherein the epigenetic modulator of FMR1 is an inhibitor of the expression of a histone methyltransferase selected from the group consisting of EZH2, SETDB1, EHMT1/GLP, EHMT2/G9a, SUV39H1, SUV420H1, and SUV420H2, and
  wherein the epigenetic modulator is an interfering nucleic acid selected from the group consisting of: double stranded RNA (dsRNA), siRNA, shRNA, miRNA, and antisense oligonucleotide (ASO).

2. The method of claim 1, wherein the FMR1-inactivation-associated disorder is fragile X syndrome, fragile X-associated tremor/ataxia syndrome, premature ovarian aging, or polycystic ovarian syndrome.

3. The method of claim 1, wherein the transcriptionally inactive FMR1 gene is epigenetically silenced or comprises at least one epigenetic mark associated with a silenced FMR1 gene.

4. The method of claim 1, wherein the subject is identified as having a FMR1-inactivation-associated disorder based upon the presence of expansion of a polymorphic CGG repeat within the 5'UTR of the FMR1 gene of the subject, optionally wherein the expansion comprises:

(i) between about 55 CGG repeats and about 200 CGG repeats; or (ii) more than 200 CGG repeats.

5. The method of claim 1, wherein the effective amount is delivered to the CNS, testes, ovaries, esophageal epithelium, thymus, eye, or spleen of the subject.

6. The method of claim 1, wherein the histone methyltransferase is SUV39H1 and the epigenetic modulator selectively inhibits SUV39H1.

7. The method of claim 1, wherein the histone methyltransferase is EZH2 and the epigenetic modulator selectively inhibits EZH2.

8. The method of claim 1, wherein the nucleic acid comprises a sequence as set forth in any one of SEQ ID NOs: 3-6.

9. The method of claim 1, wherein the effective amount is delivered to differentiated neuronal cells.

10. The method of claim 1, wherein the epigenetic modulator of FMR1 is an inhibitor of the expression of a histone methyltransferase selected from the group consisting of SETDB1, EHMT1/GLP, EHMT2/G9a, SUV39H1, SUV420H1, and SUV420H2.

\* \* \* \* \*